(12) United States Patent
Becker et al.

(10) Patent No.: US 7,189,404 B2
(45) Date of Patent: Mar. 13, 2007

(54) STRAIN SELECTION OF PNEUMOCOCCAL SURFACE PROTEINS

(75) Inventors: Robert S. Becker, Henryville, PA (US); David E. Briles, Birmingham, AL (US); Susan Hollingshead, Birmingham, AL (US)

(73) Assignee: The UAB Research Foundation, Birmingham, AL (US)

( * ) Notice: Subject to any disclaimer, the term of this patent is extended or adjusted under 35 U.S.C. 154(b) by 463 days.

(21) Appl. No.: 10/674,755

(22) Filed: Sep. 30, 2003

(65) Prior Publication Data

US 2004/0067237 A1    Apr. 8, 2004

Related U.S. Application Data

(63) Continuation of application No. 09/147,875, filed as application No. PCT/US97/16761 on Sep. 22, 1997, now Pat. No. 6,638,516, which is a continuation-in-part of application No. 08/710,749, filed on Sep. 20, 1996, now Pat. No. 5,955,089.

(51) Int. Cl.
    *A61K 39/09* (2006.01)
    *G01N 33/569* (2006.01)
    *C07K 1/00* (2006.01)
    *C07H 21/04* (2006.01)

(52) U.S. Cl. ............... 424/244.1; 424/7.34; 424/93.44; 424/165.1; 424/237.1; 530/300; 530/350; 536/23.7

(58) Field of Classification Search ............... 424/7.34, 424/93.44, 165.1, 237.1, 244.1; 530/300, 530/350; 536/23.7
See application file for complete search history.

(56) References Cited

U.S. PATENT DOCUMENTS

| 4,496,538 A | 1/1985 | Gordon |
| 4,673,574 A | 6/1987 | Anderson |
| 5,019,384 A | 5/1991 | Gefter et al. |
| 5,476,929 A | 12/1995 | Briles et al. |
| 5,679,768 A | 10/1997 | Briles et al. |
| 5,955,089 A | 9/1999 | Briles et al. |

FOREIGN PATENT DOCUMENTS

EP    0 622 081 A2    11/1994

OTHER PUBLICATIONS

Briles et al., *Microbial Drug Resistance*, 3(4):401-408 (1997).
Mufson et al., *JAMA*, 248:1486-1489 (1982).
Hook et al., *JAMA*, 249:1055-1057 (1983).
Breiman et al., *Arch. Intern. Med.*, 150:1401-1405 (1990).
Afessa et al., *Clin. Infec. Disease*, 21:345-351 (1995).
Fang et al., *Medicine*, 69:307-316 (1990).
Marie et al., *Rev. Infect. Dis.*, 11:586-599 (1989).
Torres et al., *Am. Rev. Respir. Dis.*, 144:312-318 (1991).
Bluestone et al., *Pediatr. Infect. Dis. J.*, 11:S7-S11 (1992).
Teele et al., *J. Infect. Dis.*, 1650:83-94 (1989).
Schutze et al., *Infection*, 22:233-237 (1994).
Privitera et al., *Diagnostic Microbiology and Infectious Disease*, 19:157-161 (1994).
Bizzozero et al., *Arch. Intern. Med.*, 123:388-393 (1969).
Workman et al., *Lancet*, 342:746-747 (1993).
Koornhof et al., *Clin. Infect. Dis.*, 15:84-94 (1992).
Dagan et al., *Pediatr. Infect. Dis. J.*, 13:782-786 (1994).
Reicheler et al., *J. Infect. Dis.*, 171:1491-1496 (1995).
Friedland et al., *Pediatr. Infec. Dis. J.*, 12:196-200 (1993).
Fedson et al., *Vaccines*, pp. 517-564 (1994).
Takala et al., *J. Infect. Dis.*, 164:982-986 (1993).
Takala et al., *Pediatr. Infect, Dis. J.*, 12:593-599 (1993).
Ward et al., *Vaccines*, pp. 337-386.
Murphy et al., *J. Pediatr.*, 122:517-523 (1993).
Mohle-Boetani et al., *Pediatr. Infect. Dis. J.*, 12:589-593 (1993).
Watson et al., *Infect. Immun.*, 58:3135-3138 (1990).
Avery et al., *J. Exp. Med.*, 54:73-89 (1931).
DeVelasco et al., *Microbiological Reviews*, 59:591-603 (1995).
Butler et al., *JAMA*, 270:1826-1831 (1993).
Hirschmann et al., *Arch. Intern. Med.*, 154:373-377 (1994).
Briles et al., *Rev. Infect. Dis.*, 10:S372-S374 (1988).
Talkington et al., *Microb. Pathogen*, 13:343-355 (1992).
Yother et al., *J. Bacteriol.*, 174:601-609 (1994).
Yother et al., *J. Bacteriol.*, 176:2976-2985 (1994).
McDaniel et al., *Microb. Pathog.*, 17:323-337 (1994).
Ralph et al., *A. Ann. N.Y. Acad. Sci.*, 730:361-363 (1994).
Waltman et al., *Microb. Pathog.*, 5:159-167 (1988).
McDaniel et al., *J. Exp. Med.*, 160:386-397 (1984).
McDaniel et al., *Microbial Pathogenesis*, 1:519-531 (1986).
McDaniel et al., *J. Exp. Med.*, 165:381-394 (1987).
McDaniel et al., *Infect. Immun.*, 59:222-228 (1991).
Crain et al., *Infect. Immun.*, 56:3293-3299 (1990).
Talkington et al., *Infect. Immun.*, 59:1285-1289 (1991).
Yother et al., *J. Bacteriol.*, 174:610-618 (1992).
Kuby, *Immunology*, pp. 79-81 (1992).
Bocchia et al., *Blood*, 85:2680-2684 (1994).
Englehard et al., *Ann. Rev. Immunol.*, 12:181 (1994).
Briles, "PspA's Affect on Lactoferrin Killing of Pneumococci," National Institute of Health/National Institute of Allergy and Infectious Diseases Grant No. 1RO1 AI0610 38-01, pp. 2 (2003).

*Primary Examiner*—Rodney P Swartz
(74) *Attorney, Agent, or Firm*—Nixon Peabody LLP

(57) ABSTRACT

The present invention relates to vaccine composition(s) comprising at least two PspAs from strains selected from at least one family, the family being defined by PspAs from strains belonging to the family having greater than or equal to 50% homology in aligned sequences of a C-terminal region of an alpha helical region of PspA. Additionally, the families are further comprised of clades, wherein PspAs from strains which belong to a clade exhibit greater than 75% sequence homology in aligned sequences of the C-terminal region of the alpha helix of PspA. Vaccine compositions of the present invention preferably comprise a minimum of 4 and a maximum of 6 strains representing a single clade each, and the at least two PspAs are optionally serologically or broadly cross-reactive.

34 Claims, 10 Drawing Sheets

```
Ac122a      .....LAKKQTELEK  .....LLDSLDPEGK  .....LDKEAG  EAELDKKADG  LPNKVSDLEK  EISNLEILLG
Ef3296a     LAKKQTELEK       LLDNLDPEGK       TQDELDKEAE   EAELDKKADE  LPNKVADLEK  EISNLEILLG
Bg8090a     LAKKQTELEK       LID-LDPEGK       TQDELDKEAA   EAELDKKADE  LPNKVADLEK  EISNLEILLG
Consensus   LAKKQTELEK       LID-LDPEGK       TQDELDKEA-   EAELDKKADE  LPNKVADLEK  EISNLEILLG Ac122a      GADSEDDTAA  LPNKLATKKA  ELEKTQKELD  AALNELGPDG  DEEE
Ef3296a     GADSEDDTAA  LPNKLATKKA  ELEKTQKELD  AALNELGPDG  DEEE
Bg8090a     GADPEDDTAA  LPNKLATKKA  ESEKTPKELD  AALNELGPDG  DEEE
Consensus   GADSEDDTAA  LPNKLATKKA  ELEKTQKELD  AALNELGPDG  DEEE
```

FIG. 5

```
Bg11703a   LEKAEAELEN LLSTLDPEGK TQDELDKEAA EAELNKKVEA LPNQVSELEE ELSKLEDNLK 60
Bg7817a    LEKAGAGLGN LLSTLDPEGK TQDELDKEAA EAELNKKVEA LPNQVAELEE ELSKLEDNLK 60
Ef5668a    LEDAELELEK VLATLDPEGK TQDELDKEAA EAELNEKVEA LQNQVAELEE ELSKLEDNLK 60
Bg7561a    LEKAGAGLGN LLSTLDPGGK TQDELDKGAA EAELNKKVEA LPNFVXELEE ELSPPEDNLK 60
Consensus  LEKAGAGLGN LLSTLDPEGK TQDELDKEAA EAELNKKVEA LPNQV-ELEE ELSKLEDNLK 60

Bg11703a   DAETNNVEDY IKEGLEEAIA TKQAELEKTP KELDAALNEL GPDGDEE 108
Bg7817a    DAETNHVEDY IKEGLEEAIA TKQAELEKTP KELDAALNEL GPDGDEE 108
Ef5668a    DAETNNVEDY IKEGLEEAIA TRKAELEKTQ KELDAALNEL GPDGDEE 108
Bg7561a    DAETNHVEDY IKEGLEEAIA TKQAELEETP QEVDAALNDL VPDGGEE 108
Consensus  DAETN-VEDY IKEGLEEAIA TKQAELEKTP KELDAALNEL GPDGDEE 108
```

FIG. 6

Clade 5

ATCC6303  LEDSGLGLEK  VLATLDPGGE  TPDGLDKEAS  EDSNIGALPN  QVSDLENQVS  ELDREVTRLP
          SDLKDTEGNN  VGDYVKGGLE  KALTDEKVGL               NNTPKALDTA  PKALDTALNE  LGPDGDEEE

FIG. 7

Clade 6

BG6380    QALYESTQEQ  IEELKDYNEQ  ISEGEETLIL  AIQNKISDLD  DKIAEAKKL  ADSQNGEGVE
          DYWTSGDEDK  LEKLQAEQDE  LQAELDQLLD  EVDGQE

FIG. 8

STRAIN SELECTION OF PNEUMOCOCCAL SURFACE PROTEINS

This application is a continuation of U.S. patent application Ser. No. 09/147,875, filed May 24, 1999 now U.S. Pat. No. 6,638,516, which is a continuation-in-part ("CIP") of U.S. patent application Ser. No. 08/710,749, filed Sep. 20, 1996, now U.S. Pat. No. 5,955,089, and a U.S. National Application of PCT Application No. PCT/US97/16761, filed Sep. 22, 1997, all of which are incorporated herein by their entirety.

DESCRIPTION OF DEPOSITED BIOLOGICAL MATERIALS

The *Streptococcus pneumoniae* strain designated Rx1 has been deposited pursuant to, and in satisfaction of, the requirements of the Budapest Treaty on the International Recognition of The Deposit of Microorganisms for The Purposes of Patent Procedure, with the American Type Culture Collection (ATCC), now at 10801 University Boulevard, Manassas, Va. 20110-2209, under ATCC Accession No. 55834, on Oct. 3, 1996.

BACKGROUND OF THE INVENTION

*Streptococcus pneumoniae* is an important cause of otitis media, meningitis, bacteremia and pneumonia, and a leading cause of fatal infections in the elderly and persons with underlying medical conditions such as pulmonary disease, liver disease, alcoholism, sickle cell anemia, cerebrospinal fluid leaks, acquired immune deficiency syndrome (AIDS), and patients undergoing immunosuppressive therapy. It is also a leading cause of morbidity in young children. Pneumococcal infections cause approximately 40,000 deaths in the U.S. each year. The most severe pneumococcal infections involve invasive meningitis and bacteremia infections, of which there are 3,000 and 50,000 cases annually, respectively.

Despite the use of antibiotics and vaccines, the prevalence of pneumococcal infections has declined little over the last twenty-five years; the case-fatality rate for bacteremia is reported to be 15–20% in the general population, 30–40% in the elderly, and 36% in inner-city African Americans. Less severe forms of pneumococcal disease are pneumonia, of which there are 500,000 cases annually in the U.S., and otitis media in children, of which there are an estimated 7,000,000 of such cases each year are caused by pneumococcus. Strains of drug-resistant *S. pneumoniae* are becoming ever more common in the U.S. and worldwide. In some areas, as many as 30% of pneumococcal isolates are resistant to penicillin. The increase in antimicrobial resistant pneumococcus further emphasizes the need for preventing pneumococcal infections.

Pneumococcus asymptomatically colonizes the upper respiratory tract of normal individuals; disease often results from the spread of organisms from the nasopharynx to other tissues during opportunistic events. The incidence of carriage in humans varies with age and circumstances. Carrier rates in children are typically higher than those of adults. Studies have demonstrated that 38 to 60% of preschool children, 29 to 35% of grammar school children and 9 to 25% of junior high school children are carriers of pneumococcus. Among adults, the rate of carriage drops to 6% for those without children at home, and to 18 to 29% for those with children at home. It is not surprising that the higher rate of carriage in children than in adults parallels the incidence of pneumococcal disease in these populations.

An attractive goal for streptococcal vaccination is to reduce carriage in the vaccinated populations and subsequently reduce the incidence of pneumococcal disease. There is speculation that a reduction in pneumococcal carriage rates by vaccination could reduce the incidence of the disease in non-vaccinated individuals as well as vaccinated individuals. This "herd immunity" induced by vaccination against upper respiratory bacterial pathogens has been observed using the *Haemophilus influenzae* type b conjugate vaccines (Takala, A. K., et al., *J. Infect. Dis.* 1991; 164:982–986; Takala, A. K., et al., *Pediatr. Infect. Dis. J.*, 1993; 12:593–599; Ward, J., et al., *Vaccines*, S. A. Plotkin and E. A. Mortimer, eds., 1994, pp. 337–386; Murphy, T. V., et al., *J. Pediatr.*, 1993; 122; 517–523; and Mohle-Boetani, J. C., et al., *Pediatr. Infect. Dis. J*, 1993; 12:589–593).

It is generally accepted that immunity to *Streptococcus pneumoniae* can be mediated by specific antibodies against the polysaccharide capsule of the pneumococcus. However, neonates and young children fail to make adequate immune response against most capsular polysaccharide antigens and can have repeated infections involving the same capsular serotype. One approach to immunizing infants against a number of encapsulated bacteria is to conjugate the capsular polysaccharide antigens to protein to make them immunogenic. This approach has been successful, for example, with *Haemophilus influenzae b* (see U.S. Pat. No. 4,496,538 to Gordon and U.S. Pat. No. 4,673,574 to Anderson).

However, there are over ninety known capsular serotypes of *S. pneumoniae*, of which twenty-three account for about 95% of the disease. For a pneumococcal polysaccharide-protein conjugate to be successful, the capsular types responsible for most pneumococcal infections would have to be made adequately immunogenic. This approach may be difficult, because the twenty-three polysaccharides included in the presently-available vaccine are not all adequately immunogenic, even in adults.

Protection mediated by anti-capsular polysaccharide antibody responses are restricted to the polysaccharide type. Different polysaccharide types differentially facilitate virulence in humans and other species. Pneumococcal vaccines have been developed by combining 23 different capsular polysaccharides that are the prevalent types of human pneumococcal disease. These 23 polysaccharide types have been used in a licensed pneumococcal vaccine since 1983 (D. S. Fedson and M. Musher, *Vaccines*, S. A. Plotkin and J. E. A. Montimer, eds., 1994, pp. 517–564). The licensed 23-valent polysaccharide vaccine has a reported efficacy of approximately 60% in preventing is bacteremia caused by vaccine type pneumococci in healthy adults.

However, the efficacy of the vaccine has been controversial, and at times, the justification for the recommended use of the vaccine questioned. It has been speculated that the efficacy of this vaccine is negatively affected by having to combine 23 different antigens. Having a large number of antigens combined in a single formulation may negatively affect the antibody responses to individual types within this mixture because of antigenic competition. The efficacy is also affected by the fact that the 23 serotypes encompass all serological types associated with human infections and carriage.

An alternative approach for protecting children, and also the elderly, from pneumococcal infection would be to identify protein antigens that could elicit protective immune responses. Such proteins may serve as a vaccine by themselves, may be used in conjunction with successful polysaccharide-protein conjugates, or as carriers for polysaccharides.

McDaniel et al. (I), *J. Exp. Med.* 160:386–397, 1984, relates to the production of monoclonal antibodies that recognize cell surface polypeptide(s) on *S. pneumoniae* and protection of mice from infection with certain strains of encapsulated pneumococci by such antibodies.

This surface protein antigen has been termed "pneumococcal surface protein A", or "PspA" for short.

McDaniel et al. (II), *Microbial Pathogenesis* 1:519–531, 1986, relates to studies on the characterization of the PspA. Considerable diversity in the PspA molecule in different strains was found, as were differences in the epitopes recognized by different antibodies.

McDaniel et al. (III), *J. Exp. Med.* 165:381–394, 1987, relates to immunization of X-linked immunodeficient (XID) mice with non-encapsulated pneumococci expressing PspA protects mice from subsequent fatal infection with pneumococci, but immunization with isogenic pneumococci which do not express PspA does not confer protection.

McDaniel et al. (IV), *Infect. Immun.*, 59:222–228, 1991, relates to immunization of mice with a recombinant full length fragment of PspA that is able to elicit protection against pneumococcal strains of capsular types 6A and 3.

Crain et al, *Infect.Immun.*, 56:3293–3299, 1990, relates to a rabbit antiserum that detects PspA in 100% (n=95) of clinical and laboratory isolates of strains of *S. pneumoniae*. When reacted with seven monoclonal antibodies to PspA, fifty-seven *S. pneumoniae* isolates exhibited thirty-one different patterns of reactivity.

U.S. Pat. No. 5,476,929, relates to vaccines comprising PspA and fragments thereof, methods for expressing DNA encoding PspA and fragments thereof, DNA encoding PspA and fragments thereof, the amino acid sequences of PspA and fragments thereof, compositions containing PspA and fragments thereof and methods of using such compositions.

PspA has been identified as a virulence factor and protective antigen. PspA is a cell surface molecule that is found on all clinical isolates, and the expression of PspA is required for the full virulence of pneumococci in mouse models (McDaniel et al., (III), *J. Exp. Med.* 165:381–394, 1987). The biological function of PspA has not been well defined, although a preliminary report suggests that it may inhibit complement activation (Alonso DeVelasco, E., et al., *Microbiological Rev.* 1995; 59:591–603).

The PspA protein type is independent of capsular type. It would seem that genetic mutation or exchange in the environment has allowed for the development of a large pool of strains which are highly diverse with respect to capsule, PspA, and possibly other molecules with variable structures. Variability of PspA's from different strains also is evident in their molecular weights, which range from 67 to 99 kD. The observed differences are stably inherited and are not the result of protein degradation.

Immunization with PspA in a lysate of a recombinant lgt11 clone, elicited protection against challenge with several *S. pneumoniae* strains representing different capsular and PspA types, as in McDaniel et al. (IV), *Infect. Immun.* 59:222–228, 1991. Although clones expressing PspA were constructed according to that paper, the product was insoluble and isolation from cell fragments following lysis was not possible.

Analysis of the nucleotide and amino acid sequences of the PspA molecule reveals three major regions. The first 288 amino acids at the amino terminal end of the protein are predicted to have a strong alpha helical structure. The adjacent region of 90 amino acids (289 to 369 of Rx1 PspA) has a high density of proline residues; based on similar regions in other prokaryotic proteins, this region is believed to traverse the bacterial cell wall. The remaining 196 amino acids at the carboxyl-terminal end of the molecule (370 to 588 of Rx1 PspA) have a repeated amino acid sequence that has been demonstrated to bind to phosphocholine and lipoteichoic acids. Based on this structure, the PspA molecule is thought to associate with the inner membrane and lipoteichoic acids via the repeated region in the middle of the carboxyl-terminal end of the protein. The proline region in the middle of the protein is thought to traverse the cell wall, placing the alpha helical region on the outer surface of the *S. pneumoniae* cells. This model is consistent with the demonstration that the alpha helical region, which extends from the surface of the cell, contains the protective epitopes (Yother, J. et al., *J. Bacteriol.* 1992; 174:601–609; Yother, J. et al., *J. Bacteriol.* 1994; 176:2976–2985; McDaniel, L. S. et al., *Microbial Pathog.* 1994; 17:323–337; and Ralph, B. A., et al., *Ann. N.Y. Acad. Sci.* 1994; 730: 361–363).

Serological analysis of PspA using a panel of seven monoclonal antibodies, indicated that, like capsular polysaccharides, the PspA molecules are highly diverse among pneumococcal strains. Based on these analyses, over 30 PspA protein serotypes were defined, and individual strains were assigned into groups, i.e., families (or serotypes) using a classification system based upon reactivity with the panel of monoclonal antibodies. Moreover, SDS-PAGE analysis indicated that, within a PspA serotype, further heterogeneity existed on the basis of the molecular size. This diversification further supports the assertion that PspA is a protective antigen in natural infections; the protective nature of anti-PspA responses has presumably applied selective pressure on pneumococcus to diversify this molecule. However, this diversification of the PspA molecule complicates the development of a PspA vaccine, and leads to the possibility that a PspA vaccine would have to contain many PspA strains, possibly making the vaccine impractical.

Briles et al., PCT 92/000857, used a pspA-specific probe to identify related proteins among different strains of *S. pneumoniae*. One such PspA-like polypeptide has been designated PspC. (*Abstracts of the 97th Annual Meeting of the American Societies for Microbiology*, May 1997). The gene encoding PspC hybridizes to a full-length pspA probe, demonstrating the close relatedness of the PspA and PspC proteins at the molecular level. Comparison of consensus sequences for the PspA clades with known pspC genes indicates that some of the PspC proteins can be classified within the defined PspA clades. In fact, sequence analysis of pspC genes from distinct isolates of *S. pneumoniae* reveals a greater than 85% homology at the amino acid level between the products of these pspC genes and those of pspA genes from representatives of Clade 2. Furthermore, PspC contains the same three major regions described hereinabove for PspA, namely an alpha helical N-terminal domain, a proline-rich region, and a choline binding C-terminal domain. Also, polyclonal antibodies raised against PspC cross-react with PspA proteins. Thus, for the purposes of the present invention, the term "PspA", as it appears in the specifications and in the claims appended thereto, includes full-length and truncated forms of naturally-occurring, synthetic, semi-synthetic or recombinant forms of PspA of PspC.

In addition to the published literature specifically referred to above, the inventors, in conjunction with co-workers, have published further details concerning PspAs, as follows:

1. Abstracts of 89th Annual Meeting of the American Society for Microbiology, p. 125, item D-257, May 1989;
2. Abstracts of 90th Annual Meeting of the American Society for Microbiology, p. 98, item D-106, May 1990;
3. Abstracts of 3rd International ASM Conference on Streptococcal Genetics, p. 11, item 12, June 1990;
4. Talkington et al, *Infect. Immun.* 59:1285–1289, 1991;
5. Yother et al (I), *J.Bacteriol.* 174:601–609, 1992; and
6. Yother et al (II), *J. Bacteriol.* 174:610–618, 1992.
7. McDaniel et al (V), *Microbiol. Pathogenesis*, 13:261–268, 1994.

Alternative vaccination strategies are desirable as such provide alternative routes to administration or alternative routes to generation of immune responses. It would be advantageous to provide an immunological composition or vaccination regimen which elicits protection against various diverse pneumococcal strains, without having to combine a large number of possibly competitive antigens within the same formulation.

The prior art fails to provide broadly efficacious pneumococcal vaccines. Surprisingly, the present inventions technique of clade and family groups within the Pneumococci solves this deficiency of prior art approaches by allowing a rational selection of representative PspAs from the various families of clades to produce broadly efficacious Pneumococcal vaccines, reagents and methods.

The present invention provides a vaccine composition comprising at least two PspAs from strains selected from at least two families. A family is defined by PspAs from strains having greater than or equal to 50% homology in aligned sequences of a C-terminal region of an alpha helix of PspA.

The invention provides vaccine compositions, wherein the families further comprise one or more clades. Glades are defined by PspAs having greater than 75% homology in the aligned sequences of the C-terminal region of the alpha helix of PspA.

Additionally, the present invention provides vaccine compositions wherein the C-terminal region of PspA contains epitope(s) of interest.

The present invention further provides vaccine compositions wherein a central domain comprising the C-terminal 100 amino acids of the alpha-helical region (192 to 290 of Rx1 PspA) contains epitope(s) capable of eliciting a protective response.

BRIEF DESCRIPTION OF THE FIGURES

Figure 3:
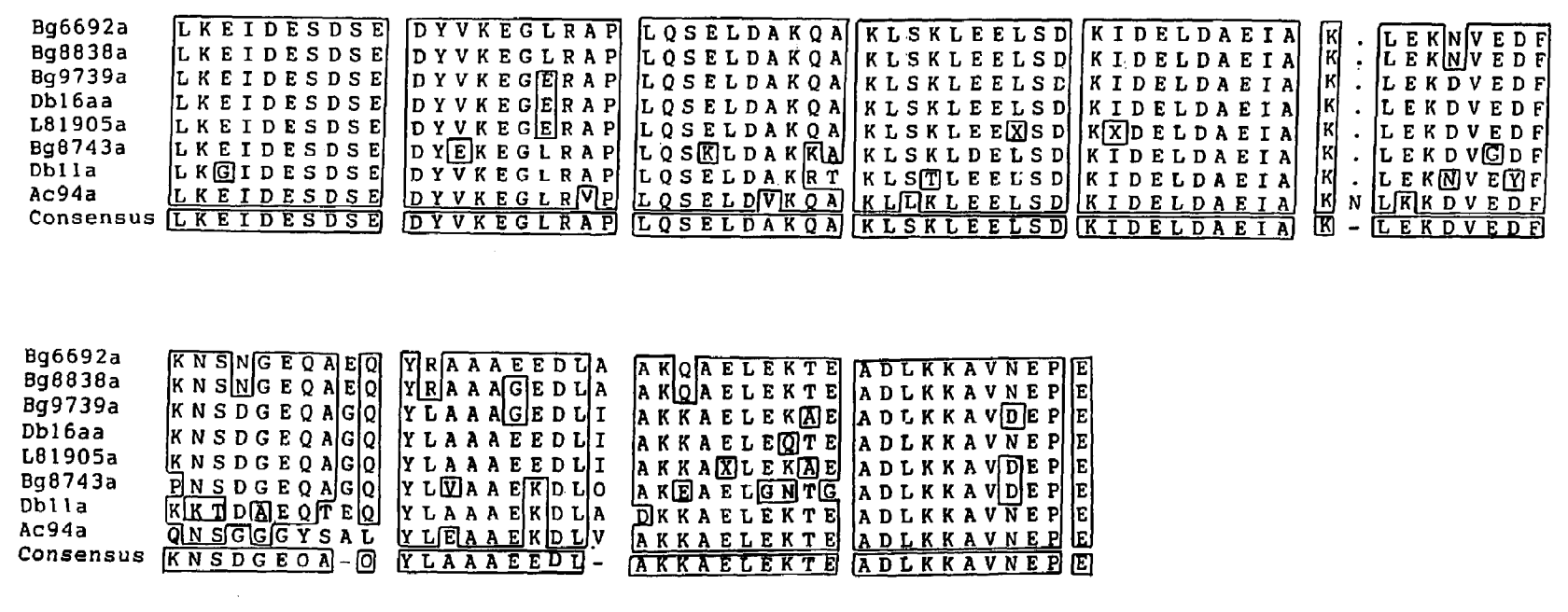

FIG. 3 shows the alignment of PspA protein amino acid sequences from the BG6692 strain (SEQ ID NO: 2), the BG8838 strain (SEQ ID NO: 3), the BG9739 strain (SEQ ID NO: 4), the DBL6A strain (SEQ ID NO: 5), the L81905 strain (SEQ ID NO: 6), the BG8743 strain (SEQ ID NO: 7), the DBL1 strain (SEQ ID NO: 8), and the AC94 strain (SEQ ID NO: 9) to the PspA clade 1 consensus sequence (SEQ ID NO: 1). FIG. 3 corresponds to the data presented in Table 3.

Figure 4:
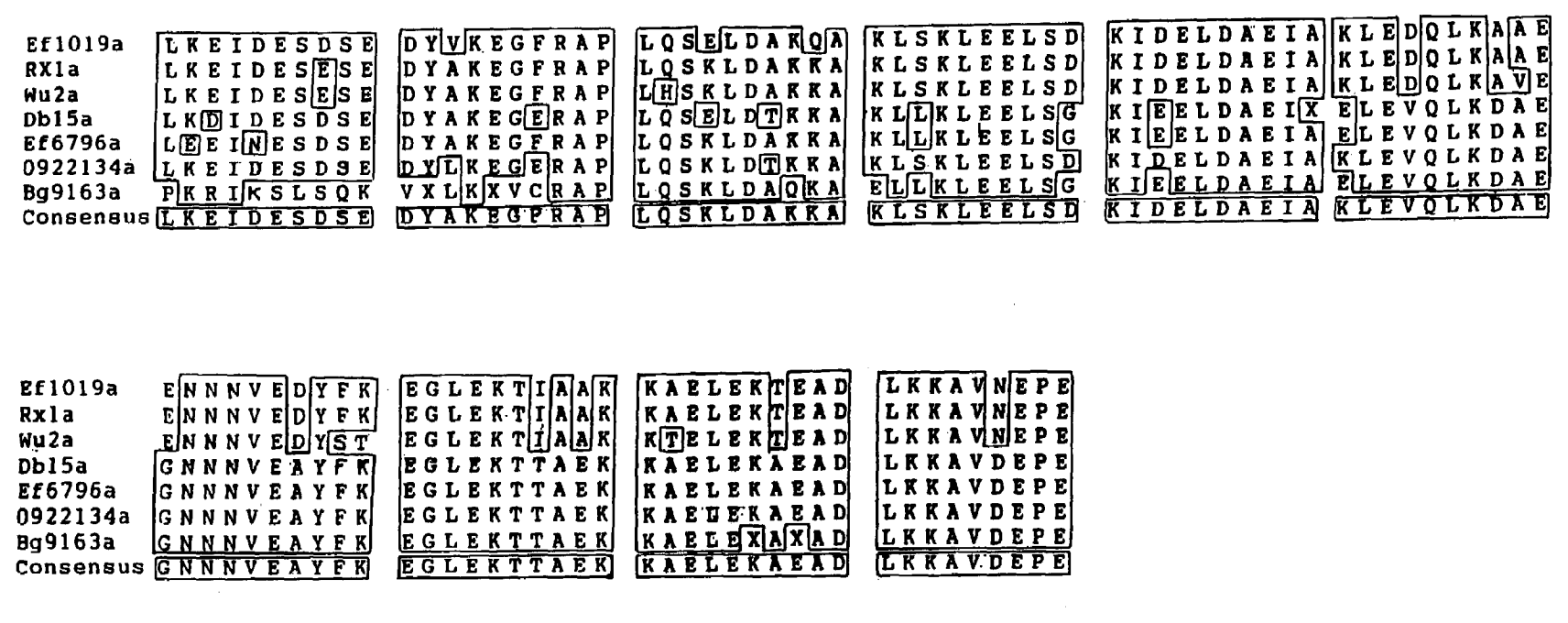

FIG. 4 shows the alignment of PspA protein amino acid sequences from the EF10197 strain (SEQ ID NO: 11), the Rx1 strain (SEQ ID NO: 12), the WU2 strain (SEQ ID NO: 13), the DBL5 strain (SEQ ID NO: 14), the EF6796 strain (SEQ ID NO: 15), the 0922134 strain (SEQ ID NO: 16), and the BG9163 strain (SEQ ID NO: 17) to the PspA clade 2 consensus sequence (SEQ ID NO: 10). FIG. 4 corresponds to the data presented in Table 4.

FIG. 5 shows the alignment of PspA protein amino acid sequences from the AC122 strain (SEQ ID NO: 19), the EF3296 strain (SEQ ID NO: 20), and the BG8090 strain (SEQ ID NO: 21) to the PspA clade 3 consensus sequence (SEQ ID NO: 18). FIG. 5 corresponds to the data presented in Table 5.

FIG. 6 shows the alignment of PspA protein amino acid sequences from the BG11703 strain (SEQ ID NO: 23), the BG7817 strain (SEQ ID NO: 24), the EF5668 strain (SEQ ID NO: 25), and the BG7561 strain (SEQ ID NO: 26) to the PspA clade 4 consensus sequence (SEQ ID NO: 22). FIG. 6 corresponds to the data presented in Table 6.

FIG. 7 shows the amino acid sequence of PspA from strain ATCC6303 (SEQ ID NO: 27), a representative strain of clade 5.

FIG. 8 shows the amino acid sequence of PspA from strain BG6380 (SEQ ID NO: 28), a representative strain of clade 6.

DETAILED DESCRIPTION

Figure 1:
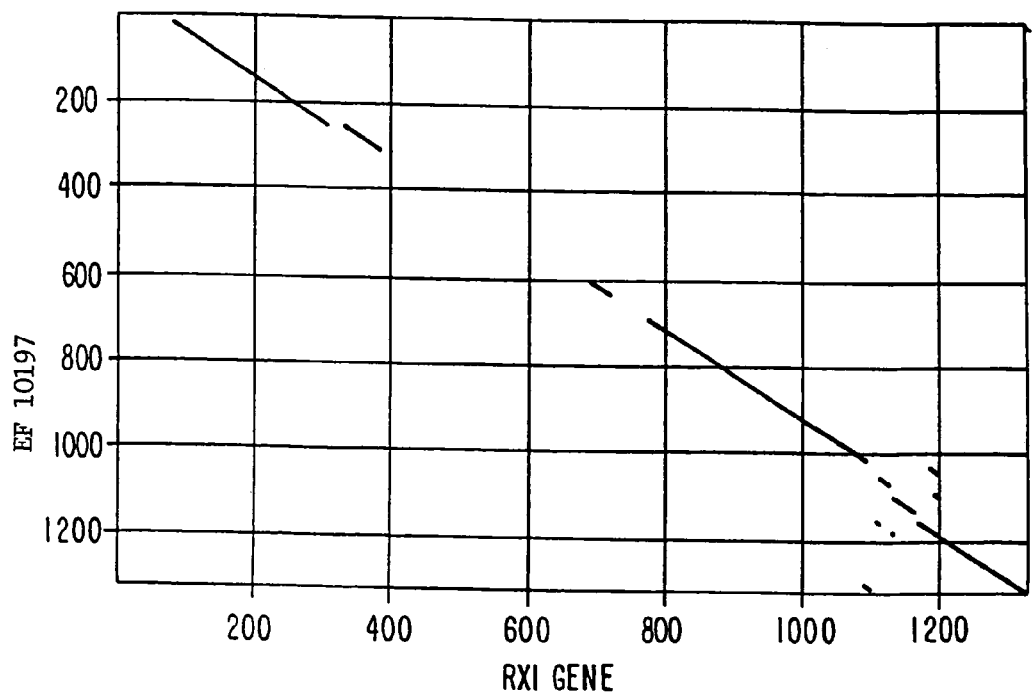
FIG. 1 shows a Pustell DNA matrix analysis of homology between the PspA genes of Rx1 and EF10197 strains.
Figure 2:
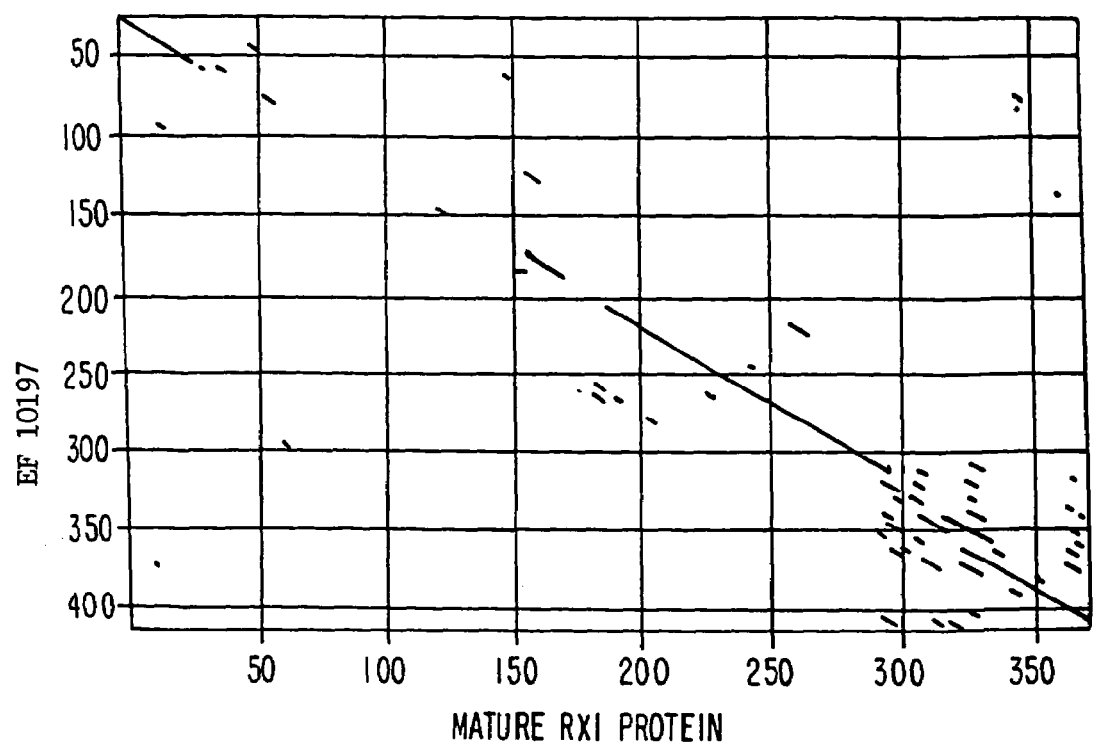
FIG. 2 shows a Pustell protein matrix analysis of homology between the PspA proteins of Rx1 and EF10197 strains.

It has now been surprisingly found that, despite the assertions of the prior art regarding the apparent diversity of PspA from strains, the primary sequence of the alpha helix of PspA has two regions of relative conservation and a region of extensive diversity between PspAs from stains. The two regions of relative conservation are comprised of the first, N-terminal, 60 amino acids of the alpha helix, and the last, C-terminal, about 100 amino acids of the alpha helix, as shown in FIGS. 1 and 2, wherein the C-terminal end of the alpha helix contains cross-reactive and protective epitopes that are critical to the development of a broadly efficacious PspA vaccine. It has been found that any conservation in the first, N-terminal, 60 amino acids of the alpha helix is of little consequence in the cross-reactivity of the strain, and hence, is irrelevant to the development of a PspA vaccine.

A comparison of the amino acid sequences in the C-terminal region of the alpha helix of PspAs from 24 strains of *S. pneumoniae* has revealed that the PspA strains can be grouped into 6 clades with greater than 75% homology, and these clades can be grouped into 4 families with greater than 50% homology.

Accordingly, the present invention provides a method of strain selection of PspA, based upon the sequence homology of PspAs in the C-terminal region of the alpha helix.

A clade is defined herein as comprising PspAs which exhibit greater than 75% sequence homology in aligned sequences of the C-terminal region of the alpha helix, and family is defined herein as those clades which exhibit greater than or equal to 50% homology between member PspA sequences in aligned sequences of the C-terminal region of the alpha helix.

Further, it has been found that in addition to sequence homology, members of a clade exhibit cross-reactivity and cross-protection among one another, which may suggest a causal relationship between sequence homology and cross-reactivity. PspAs of strains within the same PspA clade exhibit reciprocal cross-protection from immunization and challenge experiments. It has not been heretofore recognized in the prior art that there may be such a causal relationship; in fact, families of PspA strains were defined solely on the basis of serological cross-reactivity and, based upon the prior art definition of families of PspA strains, it was believed that the extreme diversity of the PspA molecule would result in a futile attempt at strain selection. Moreover, the PspA typing system (Crain, et al., *Infect. Immun.* 59: 222–228, 1990) failed to provide relevant groupings of strains, and suggested an enormous diversity.

Hence, the present invention, in contrast to the teachings of the prior art, enables the selection of PspAs from strains in accordance with sequence homology and cross-reactivity, which facilitates the development of vaccine compositions comprising multiple PspAs.

The present invention contemplates vaccine compositions comprising two or more, preferably no more than 10, and more preferably a minimum of 4 and a maximum 6 strains of PspA representing a single clade each, and a pharmaceutically acceptable carrier or diluent. In a preferred embodiment, Rx1, a member of clade 2, is the preferred strain of clade 2 and/or family 1 which is optionally included in the vaccine composition of the present invention.

The aforementioned definition of a family structure to the C-terminal end of the alpha helix region enables the development of a broadly efficacious pneumococcal vaccine composition with a limited number of strains. Combining strains that represent some or all of the families for this cross-reactive and protective region should provide broad protection against pneumococcal disease. Not all clades may need to be represented because of cross-reactions between some clades within families or because of the epidemiology of these strains or clades in the population to be vaccinated. However, it is well within the scope of knowledge of the skilled artisan to determine those strains which should be included within a vaccine composition, without the burden of undue experimentation. Additionally, the selected PspAs and PspA-like polypeptides of the present invention further contain epitope(s) of interest which can elicit an immune response. An epitope of interest is that portion of an antigen or immunogen of interest which is capable of interacting with an antibody or T cell.

The present invention provides an immunogenic, immunological or vaccine composition containing pneumococcal strain(s) having an epitope of interest, and a pharmaceutically acceptable carrier or diluent. An immunological composition containing the PspAs having an epitope of interest, elicits an immunological response—local or systemic. The response can, but need not be, protective. An immunogenic composition containing the PspAs having an epitope of interest, likewise elicits a local or systemic immunological response which can, but need not be, protective. A vaccine composition elicits a local or systemic protective response. Accordingly, the terms "immunological composition" and "immunogenic composition" include a "vaccine composition" (as the two former terms can be protective compositions).

The invention therefore also provides a method of inducing an immunological response in a host mammal comprising administering to the host an immunogenic, immunological or vaccine composition comprising PspAs having an epitope of interest, and a pharmaceutically acceptable carrier or diluent. As to epitopes of interest, one skilled in the art can often identify epitopes or immunodominant regions of a peptide or polypeptide, and ergo, the coding DNA therefor from the knowledge of the amino acid and corresponding DNA sequences of the peptide or polypeptide, as well as from the nature of particular amino acids (e.g., size, charge, etc.) and the codon dictionary, without undue experimentation.

A general method for determining which portions of a protein to use in an immunological composition focuses on the size and sequence of the antigen of interest. "In general, large proteins, because they have more potential determinants are better antigens than small ones. The more foreign an antigen, that is the less similar to self configurations which induce tolerance, the more effective it is in provoking an immune response." Ivan Roitt, *Essential Immunology*, 1988.

At a minimum, such a peptide must be at least 8 or 9 amino acids long. This is the minimum length that a peptide needs to be in order to stimulate a CD4+ T cell response (which recognizes virus infected cells or cancerous cells). A minimum peptide length of 13 to 25 amino acids is useful to stimulate CD8+ T cell response (which recognizes special antigen presenting cells which have engulfed the pathogen). See Kendrew, supra. However, as these are minimum lengths, these peptides are likely to generate an immunological response, i.e., an antibody or T cell response; but, for a protective response (as from a vaccine composition), a longer peptide is preferred.

With respect to the sequence, the DNA sequence encoding the immunogenic peptide preferably encodes at least regions of the peptide that generate an antibody response or a T cell response. One method to determine T and B cell epitopes involves epitope mapping. The protein of interest "is fragmented into overlapping peptides with proteolytic enzymes. The individual peptides are then tested for their ability to bind to an antibody elicited by the native protein or to induce T cell or B cell activation. This approach has been particularly useful in mapping T-cell epitopes since the T cell recognizes short linear peptides complexed with MHC molecules. The method is less effective for determining B-cell epitopes" since B cell epitopes are often not linear amino acid sequence but rather result from the tertiary structure of the folded three dimensional protein. Janis Kuby, *Immunology*, pp. 79–80 (1992).

In the case of PspA, the location of the major cross-reactive region at the C-terminal 100 amino acids of the alpha-helical region was carried out with recombinant peptides of 100 or more amino acids in length (McDaniel et al., *Micro. Pathog.* 17:323–337, 1994).

Another method for determining an epitope of interest is to choose the regions of the protein that are hydrophilic. Hydrophilic residues are often on the surface of the protein and therefore often the regions of the protein which are accessible to the antibody. Janis Kuby, *Immunology*, p. 81 (1992).

Yet another method for determining an epitope of interest is to perform an X-ray crystallographic analysis of the antigen (full length)-antibody complex. Janis Kuby, *Immunology*, p. 80 (1992).

An immune response is generated, in general, as follows: T cells recognize proteins only when the protein has been cleaved into smaller peptides, which are then presented to the T cells in a complex called the major histocompatability complex ("MHC") located on another cell's surface. There are two classes of MHC complexes—class I and class II, and each class is made up of many different alleles. Different patients have different types of MHC complex alleles; they are said to have a different "HLA type".

Class I MHC complexes are found on virtually every cell and present peptides from proteins produced inside the cell.

Thus, Class I MHC complexes are useful for killing cells which have been infected by viruses or which have become cancerous and as the result of expression of an oncogene. T cells which have a protein called CD4 on their surface bind to the MHC class I cells and secrete lymphokines. The lymphokines stimulate a response; cells arrive and kill the virus-infected cell. Class II MHC complexes are found only on antigen-presenting cells and are used to present peptides from circulating pathogens which have been endocytosed by the antigen-presenting cells. T cells which have a protein called CD8 bind to the MHC class II cells and kill the cell by exocytosis of lytic granules.

Thus, another method for identifying epitopes of interest is to identify those regions of the protein which can generate a T cell response. In order to generate a T cell response, a peptide which comprises a putative epitope should be presented in the context of a MHC complex. Those skilled in the art can identify from the protein sequence of the antigen of interest potential human lymphocyte antigen ("HLA") anchor binding motifs. HLA anchor binding motifs are peptide sequences which are known to be likely to bind to the MHC molecule. The peptide preferably contains appropriate anchor motifs for binding to the MHC molecules, and should bind with high enough affinity to generate an immune response. Other factors which can be considered are: the HLA type of the patient (vertebrate, animal or human) expected to be immunized, the sequence of the protein, the presence of appropriate anchor motifs and the occurrence of the peptide sequence in other vital cells.

Some guidelines in determining whether a protein contains epitopes of interest capable of stimulating a T cell response, include: Peptide length—the peptide should be at least 8 or 9 amino acids long to fit into the MHC class I complex and at least 13–25 amino acids long to fit into a class II MHC complex. This length is a minimum for the peptide to bind to the MHC complex. It is preferred for the peptides to be longer than these lengths because cells may cut the expressed peptides. The peptide should contain an appropriate anchor motif which will enable it to bind to the various class I or class II molecules with high enough specificity to generate an immune response (See Bocchia, M. et al, "Specific Binding of Leukemia Oncogene Fusion Protein Peptides to HLA Class I Molecules," *Blood* 85:2680–2684; Englehard, V H, "Structure of Peptides Associated with Class I and Class II MHC Molecules," *Ann. Rev. Immunol.* 12:181 (1994)). This can be done, without undue experimentation, by comparing the sequence of the protein of interest with published structures of peptides associated with the MHC molecules. Protein epitopes recognized by T cell receptors are peptides generated by enzymatic degradation of the protein molecule and are presented on the cell surface in association with class I or class II MHC molecules.

Further, the skilled artisan can ascertain an epitope of interest by comparing the protein sequence with sequences listed in the protein data base. Regions of the protein which share little or no homology are better choices for being an epitope of that protein and are therefore useful in a vaccine or immunological composition. Regions which share great homology with widely found sequences present in vital cells should be avoided.

Even further, another method is simply to generate or express portions of a protein of interest, generate monoclonal antibodies to those portions of the protein of interest, and then ascertain whether those antibodies inhibit growth in vitro of the pathogen from which the protein was derived. The skilled artisan can use the other guidelines set forth in this disclosure and in the art for generating or expressing portions of a protein of interest for analysis as to whether antibodies thereto inhibit growth in vitro. For example, the skilled artisan can generate portions of a protein of interest by: selecting 8 to 9 or 13 to 25 amino acid length portions of the protein, selecting hydrophilic regions, selecting portions shown to bind from X-ray data of the antigen (full length)-antibody complex, selecting regions which differ in sequence from other proteins, selecting potential LA anchor binding motifs, or any combination of these methods or other methods known in the art.

Epitopes recognized by antibodies are expressed on the surface of a protein. To determine the regions of a protein most likely to stimulate an antibody response one skilled in the art can preferably perform an epitope map, using the general methods described above, or other mapping methods known in the art.

As can be seen from the foregoing, without undue experimentation, from this disclosure and the knowledge in the art, the skilled artisan can ascertain the amino acid and corresponding DNA sequence of an epitope of interest for obtaining a T cell, B cell and/or antibody response. In addition, reference is made to Defter et al., U.S. Pat. No. 5,019,384, issued May 28, 1991, and the documents it cites, incorporated herein by reference (Note especially the "Relevant Literature" section of this patent, and column 13 of this patent which discloses that: "A large number of epitopes have been defined for a wide variety of organisms of interest. Of particular interest are those epitopes to which neutralizing antibodies are directed. Disclosures of such epitopes are in many of the references cited in the Relevant Literature section.")

Further, the invention demonstrates that more than one serologically complementary PspA molecule can be in an antigenic, immunological or vaccine composition, so as to elicit better response, e.g., protection, for instance, against a variety of strains of pneumococci; and, the invention provides a system of selecting PspAs for a multivalent composition which includes cross-protection evaluation so as to provide a maximally efficacious composition. The determination of the amount of antigen, e.g., PspA or truncated portion thereof and optional adjuvant in the inventive compositions and the preparation of those compositions can be in accordance with standard techniques well known to those skilled in the pharmaceutical or veterinary arts. In particular, the amount of antigen and adjuvant in the inventive compositions and the dosages administered are determined by techniques well known to those skilled in the medical or veterinary arts taking into consideration such factors as the particular antigen, the adjuvant (if present), the age, sex, weight, species and condition of the particular animal or patient, and the route of administration. For instance, dosages of particular PspA antigens for suitable hosts in which an immunological response is desired, can be readily ascertained by those skilled in the art from this disclosure, as is the amount of any adjuvant typically administered therewith. Thus, the skilled artisan can readily determine the amount of antigen and optional adjuvant in compositions and to be administered in methods of the invention. Typically, an adjuvant is commonly used as 0.001 to 50 wt % solution in phosphate buffered saline, and the antigen is present on the order of micrograms to milligrams, such as about 0.0001 to about 5 wt %, preferably about 0.0001 to about 1 wt %, most preferably about 0.0001 to about 0.05 wt % (see, e.g., Examples below or in applications cited herein). Typically, however, the antigen is present in an amount on the order of micrograms to milligrams, or, about 0.001 to about 20 wt %, preferably about 0.01 to about 10 wt %, and most preferably about 0.05 to about 5 wt %.

Of course, for any composition to be administered to an animal or human, including the components thereof, and for any particular method of administration, it is preferred to determine therefor: toxicity, such as by determining the lethal dose (LD) and $LD_{50}$ in a suitable animal model e.g., rodent such as mouse; and, the dosage of the composition(s), concentration of components therein and timing of administering the composition(s), which elicit a suitable immunological response, such as by titrations of sera and analysis thereof for antibodies or antigens, e.g., by ELISA and/or RFFIT analysis. Such determinations do not require undue experimentation from the knowledge of the skilled artisan, this disclosure and the documents cited herein. And, the time for sequential administrations can be ascertained without undue experimentation.

Examples of compositions of the invention include liquid preparations for orifice, e.g., oral, nasal, anal, vaginal, peroral, intragastric, mucosal (e.g., perlingual, alveolar, gingival, olfactory or respiratory mucosa) etc., administration such as suspensions, syrups or elixirs; and, preparations for parenteral, subcutaneous, intradermal, intramuscular or intravenous administration (e.g., injectable administration), such as sterile suspensions or emulsions. Such compositions may be in admixture with a suitable carrier, diluent, or excipient such as sterile water, physiological saline, glucose or the like. The compositions can also be lyophilized. The compositions can contain auxiliary substances such as wetting or emulsifying agents, pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation.

Compositions of the invention are conveniently provided as liquid preparations, e.g., isotonic aqueous solutions, suspensions, emulsions or viscous compositions which may be buffered to a selected pH. If digestive tract absorption is preferred, compositions of the invention can be in the "solid" form of pills, tablets, capsules, caplets and the like, including "solid" preparations which are time-released or which have a liquid filling, e.g. gelatin covered liquid, whereby the gelatin is dissolved in the stomach for delivery to the gut. If nasal or respiratory (mucosal) administration is desired, compositions may be in a form and dispensed by a squeeze spray dispenser, pump dispenser or aerosol dispenser. Aerosols are usually under pressure by means of a hydrocarbon. Pump dispensers can preferably dispense a metered dose or a dose having a particular particle size.

Compositions of the invention can contain pharmaceutically acceptable flavors and/or colors for rendering them more appealing, especially if they are administered orally. The viscous compositions may be in the form of gels, lotions, ointments, creams and the like and will typically contain a sufficient amount of a thickening agent so that the viscosity is from about 2500 to 6500 cps, although more viscous compositions, even up to 10,000 cps may be employed. Viscous compositions have a viscosity preferably of 2500 to 5000 cps, since above that range they become more difficult to administer. However, above that range, the compositions can approach solid or gelatin forms which are then easily administered as a swallowed pill for oral ingestion.

Liquid preparations are normally easier to prepare than gels, other viscous compositions, and solid compositions. Additionally, liquid compositions are somewhat more convenient to administer, especially by injection or orally, to animals, children, particularly small children, and others who may have difficulty swallowing a pill, tablet, capsule or the like, or in multi-dose situations. Viscous compositions, on the other hand, can be formulated within the appropriate viscosity range to provide longer contact periods with mucosa, such as the lining of the stomach or nasal mucosa.

Obviously, the choice of suitable carriers and other additives will depend on the exact route of administration and the nature of the particular dosage form, e.g., liquid dosage form (e.g., whether the composition is to be formulated into a solution, a suspension, gel or another liquid form), or solid dosage form (e.g., whether the composition is to be formulated into a pill, tablet, capsule, caplet, time release form or liquid-filled form).

Solutions, suspensions and gels, normally contain a major amount of water (preferably purified water) in addition to the antigen, and optional adjuvant. Minor amounts of other ingredients such as pH adjusters (e.g., a base such as NaOH), emulsifiers or dispersing agents, buffering agents, preservatives, wetting agents, jelling agents, (e.g., methylcellulose), colors and/or flavors may also be present. The compositions can be isotonic, i.e., it can have the same osmotic pressure as blood and lacrimal fluid.

The desired isotonicity of the compositions of this invention may be accomplished using sodium chloride, or other pharmaceutically acceptable agents such as dextrose, boric acid, sodium tartrate, propylene glycol or other inorganic or organic solutes. Sodium chloride is preferred particularly for buffers containing sodium ions.

Viscosity of the compositions may be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the agent selected. The important point is to use an amount which will achieve the selected viscosity. Viscous compositions are normally prepared from solutions by the addition of such thickening agents.

A pharmaceutically acceptable preservative can be employed to increase the shelf-life of the compositions. Benzyl alcohol may be suitable, although a variety of preservatives including, for example, parabens, thimerosal, chlorobutanol, or benzalkonium chloride may also be employed. A suitable concentration of the preservative will be from 0.02% to 2% based on the total weight although there may be appreciable variation depending upon the agent selected.

Those skilled in the art will recognize that the components of the compositions must be selected to be chemically inert with respect to the PspA antigen and optional adjuvant. This will present no problem to those skilled in chemical and pharmaceutical principles, or problems can be readily avoided by reference to standard texts or by simple experiments (not involving undue experimentation), from this disclosure and the documents cited herein.

The immunologically effective compositions of this invention are prepared by mixing the ingredients following generally accepted procedures. For example the selected components may be simply mixed in a blender, or other standard device to produce a concentrated mixture which may then be adjusted to the final concentration and viscosity by the addition of water or thickening agent and possibly a buffer to control pH or an additional solute to control tonicity. Generally the pH may be from about 3 to 7.5. Compositions can be administered in dosages and by techniques well known to those skilled in the medical and veterinary arts taking into consideration such factors as the age, sex, weight, and condition of the particular patient or animal, and the composition form used for administration (e.g., solid vs. liquid). Dosages for humans or other animals can be determined without undue experimentation by the skilled artisan from this disclosure, the documents cited herein and the Examples below (e.g., from the Examples involving mice).

Suitable regimes for initial administration and booster doses or for sequential administrations also are variable, may include an initial administration followed by subsequent administrations; but nonetheless, may be ascertained by the skilled artisan from this disclosure, the documents cited herein and the Examples below.

The following Examples are provided for illustration and are not to be considered a limitation of the invention.

EXAMPLES

Example 1

Identification of Sequence Homologies Between PspAs

Despite the described diversity of PspA strains, the nucleotide and amino acids sequences of the PspA molecule has been evaluated with respect to whether any region(s) of conservation have been maintained which could be of utility to vaccine development. The comparison of the nucleotide and amino acid sequences from multiple strains of PspA revealed that the primary sequence of the alpha helix has two regions of relative conservation and a region of extensive diversity between strains. The two regions of diversity are comprised of the first, N-terminal, 60 amino acids of the alpha helix, and the last, C-terminal, 100 amino acids of the alpha helix, as shown in FIGS. 1 and 2.

FIG. 1 shows the nucleotide sequences of the alpha helix and proline regions of the pspA genes from Rx1 and EF10197, both members of the same family or clade, as compared to each other for regions of homology. This comparison was made using a Pustell DNA matrix analysis within the MacVector version 5.0.2 software, using a window of 30 nucleotides, a minimum percentage of homology of 70%, a hash value of 6, and a jump value of 1. Points or lines in the graph indicate regions of homology between the two genes that meet the aforementioned criteria. The results demonstrate homology in the portions of the genes encoding the N-terminal and C-terminal ends of the alpha helix region, as well as the proline region.

FIG. 2 shows the amino acid sequence comparison of the alpha helix and proline regions of the PspA proteins from Rx1 and EF10197, both members of the same family or clade, as compared to each other for regions of homology. This comparison was made using a Pustell protein matrix analysis within the MacVector version 5.0.2 software. The analysis was done using a window of 8 amino acids, a minimum percentage homology of 70%, a hash value of 2, and the pam250 scoring matrix. Points or lines in the graph indicate regions of homology between the two proteins. The results demonstrate homology in the N-terminal and the C-terminal ends of the alpha helix region, as well as in the proline region.

The conserved region at the C-terminal end of the alpha helix region correlated with a region demonstrated to contain protective epitopes that were conserved between two strains.

Reasoning that the C-terminal region of the alpha helix region was critical to vaccine development, the heterogeneity and family structure of amino acid sequences in this region was examined. The comparison of the amino acid sequences in this region between 26 strains of PspA revealed that the PspA strains could be grouped into 6 clades with greater than 75% homology. These clades could be grouped into 4 families with greater than 50% homology. These data are shown in Tables 1 to 6, and FIGS. 3 to 8.

TABLE 1

Family/Clade List

| FAMILY | HOMOL-OGY WITHIN FAMILY | CLADE | STRAIN | % AMINO ACID HOMOLOGY TO CLADE CONSENSUS |
|---|---|---|---|---|
| Family 1 | >50% | Clade 1 (SEQ ID NO:1) | BG9739 (SEQ ID NO:4) | 96 |
| | | | DBL6A (SEQ ID NO:5) | 98 |
| | | | L81905 (SEQ ID NO:6) | 94 |
| | | | BG8743 (SEQ ID NO:7) | 87 |
| | | | AC94 (SEQ ID NO:9) | 88 |
| | | | BG6692 (SEQ ID NO:2) | 96 |
| | | | BG8838 (SEQ ID NO:3) | 95 |
| | | | DBL1 (SEQ ID NO:8) | 88 |
| | | Clade 2 (SEQ ID NO:10) | EF10197 (SEQ ID NO:11) | 89 |
| | | | RX1 (SEQ ID NO:12) | 92 |
| | | | WU2 (SEQ ID NO:13) | 87 |
| | | | 0922134 (SEQ ID NO:16) | 99 |
| | | | DBL5 (SEQ ID NO:14) | 92 |
| | | | BG9163 (SEQ ID NO:17) | 79 |
| | | | EF6796 (SEQ ID NO:15) | 91 |
| Family 2 | >50% | Clade 3 (SEQ ID NO:18) | EF3296 (SEQ ID NO:20) | 97 |
| | | | AC122 (SEQ ID | 96 |

TABLE 1-continued

Family/Clade List

| FAMILY | HOMOLOGY WITHIN FAMILY | CLADE | STRAIN | % AMINO ACID HOMOLOGY TO CLADE CONSENSUS |
|---|---|---|---|---|
| | | | NO:19) | |
| | | | BG8090 (SEQ ID NO:21) | 96 |
| Family 3 | >50% | Clade 4 (SEQ ID NO:22) | EF5668 (SEQ ID NO:25) | 92 |
| | | | BG7817 (SEQ ID NO:24) | 96 |
| | | | BG7561 (SEQ ID NO:26) | 89 |
| | | | BG11703 (SEQ ID NO:23) | 100 |
| | | Clade 5 | ATCC6303 (SEQ ID NO:27) | 100 |
| Family 4 | >50% | Clade 6 | BG6380 (SEQ ID NO:28) | 100 |

TABLE 2A

Homology Between Clades - Matrix of Amino Acid Similarity Estimates Between Clades

| | Clade 1 | Clade 2 | Clade 3 | Clade 4 | Clade 5 | Clade 6 |
|---|---|---|---|---|---|---|
| Clade 1 | >75% | | | | | |
| Clade 2 | >50% | >75% | | | | |
| Clade 3 | <25% | <20% | >75% | | | |
| Clade 4 | <20% | >30% | >30% | >75% | | |
| Clade 5 | <20% | <20% | >30% | >50% | >75% | |
| Clade 6 | <10% | <20% | <10% | <20% | <20% | >75% |

TABLE 2B

AA % sequence identities to PspA Clade Consensus

| Clade | Strain Name (Capsular Type) | % of AA that differ from the Clade Consensus | % AA identity to Clade Consensus |
|---|---|---|---|
| Clade 1 | BG9739 (4) | 4 | 96 |
| | DBL6A (6A) | 2 | 98 |
| | L81905 (4) | 6 | 94 |
| | BG8743 (23) | 13 | 87 |
| | AC94 (9) | 12 | 88 |
| | BG6692 (33) | 4 | 96 |
| | BG8838 (6) | 5 | 95 |
| | DBL1 (6B) | 12 | 88 |
| Clade 2 | EF10197 (3) | 10 | 89 |
| | RX1 (2) | 8 | 92 |
| | WU2 (3) | 13 | 87 |
| | 0922134 (23) | 1 | 99 |
| | DBL5 (5) | 8 | 92 |
| | BG9163 (6B) | 21 | 79 |
| | EF6796 (6A) | 9 | 91 |
| Clade 3 | EF3296 (4) | 1 | 97 |
| | AC122 (9) | 2 | 96 |
| | BG8090 (19) | 4 | 96 |
| Clade 4 | EF5668 (4) | 9 | 92 |
| | BG7817 (7) | 4 | 96 |
| | BG7561 (15) | 12 | 89 |
| | BG11703 (N.D) | 0 | 100 |
| Clade 5 | ATCC6303 (3) | 0 | 100 |
| Clade 6 | BG6380 (37) | 0 | 100 |

N.D. = not determined

TABLE 3

Sequence identities to PspA Clade 1 Consensus

| CLADE | STRAIN NAME | # OF AA THAT DIFFER FROM THE CLADE CONSENSUS | % AA IDENTITY TO CLADE CONSENSUS |
|---|---|---|---|
| Clade 1 | BG9739 | 4 | 96 |
| | DBL6A | 2 | 98 |
| | L81905 | 6 | 94 |
| | BG8743 | 13 | 87 |
| | AC94 | 12 | 88 |
| | BG6692 | 4 | 96 |
| | BG8838 | 5 | 95 |
| | DBL1 | 12 | 88 |

TABLE 4

Sequence identities to PspA Clade 2 consensus

| CLADE | STRAIN NAME | # OF AA THAT DIFFER FROM THE CLADE CONSENSUS | % AA IDENTITY TO CLADE CONSENSUS |
|---|---|---|---|
| Clade 2 | EF10197 | 10 | 89 |
| | RX1 | 8 | 92 |
| | WU2 | 13 | 87 |
| | 0922134 | 1 | 99 |
| | DBL5 | 8 | 92 |
| | BG9163 | 21 | 79 |
| | EF6796 | 9 | 91 |
| | RCT123 | 3 | 97 |
| | RCT129 | 1 | 99 |
| | RCT135 | 0 | 100 |
| | LXS200 | 0 | 100 |

TABLE 5

Sequence identities to PspA Clade 3 Consensus

| CLADE | STRAIN NAME | # OF AA THAT DIFFER FROM THE CLAD CONSENSUS | % AA IDENTITY TO CLADE CONSENSUS |
|---|---|---|---|
| Clade 3 | EF3296 | 1 | 97 |
| | AC122 | 2 | 96 |
| | BG8090 | 4 | 96 |

TABLE 6

Sequence identities to PspA Clade 4 Consensus

| CLADE | STRAIN NAME | # OF AA THAT DIFFER FROM THE CLAD CONSENSUS | % AA IDENTITY TO CLADE CONSENSUS |
|---|---|---|---|
| Clade 4 | EF5668 | 9 | 92 |
| | BG7817 | 4 | 96 |
| | BG7561 | 12 | 89 |
| | BG11703 | 0 | 100 |

The immnunological relevance of these families was demonstrated by serological analysis of *S. pneumoniae* strains with a large number of monoclonal antibodies made to several different PspAs. As shown in Table 7, the pattern of reactions with strains in clades 3, 4, 5 and 6 of monoclonal antibodies generally correlated with the defined clade by sequence.

TABLE 7

Ab Reactions Clades 3–6

Anti-PspA Monoclonal Antibodies

| STRAIN | CLADE* | Made to EF3296(P32) | | | | Made to EF5668(P56) | | | |
|---|---|---|---|---|---|---|---|---|---|
| | | 263D12 | 263F6 | 264A4 | 264A11 | 265E6 | 270B6 | 263B7 | 351G12 |
| EF3296 | 3 | X | X | X | X | X | X | X | |
| BG7140 | | X | | X | X | X | X | | |
| PMsv1281 | | X | X | X | X | | X | X | |
| VH1193 | | X | X | X | X | X | X | X | |
| EF5668 | 4 | | | | | | | | X |
| BG7817 | 4 | | | | | | | | X |
| BG7561 | 4 | | | | | | | | X |
| BG11703 | 4 | | | | | | | | X |
| BG7736 | | | | | | | | | X |
| BG7813 | | | | | | | | | X |
| BG7915 | | | | | | | | | X |
| BG10717-/30 | | | | | | | | | X |
| ATCC6-306 | 5 | | | | | | | | X |
| BG7619 | | | | | | | | | X |
| BG7941 | | | | | | | | | X |
| BG13075-/30 | | | | | | | | | X |
| BG6380 | 6 | | | | | | | | |

X indicates a positive reaction
*clade was determined by amino acid sequences

Figure 9:
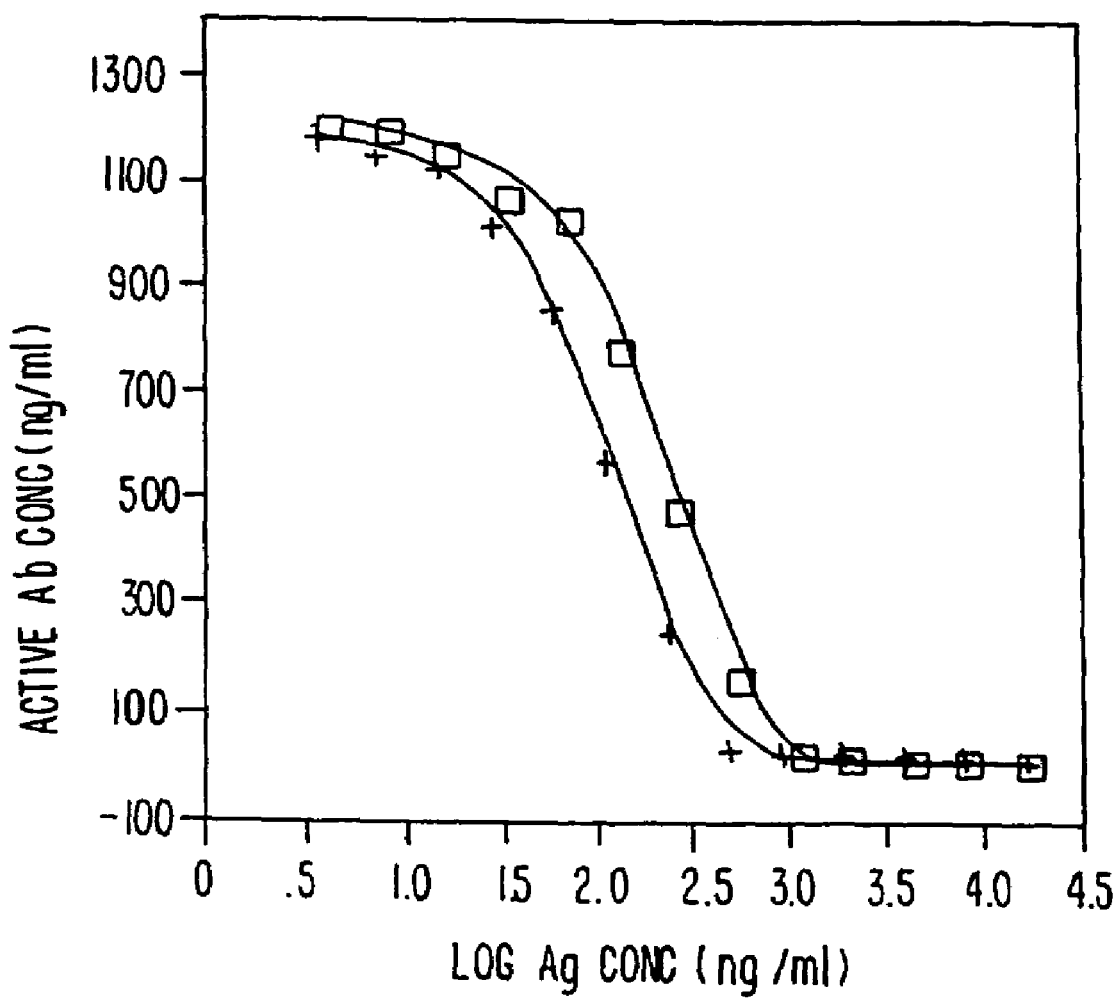
FIG. 9 shows the competitive inhibition of rabbit polyclonal anti-Rx1 by PA314, recombinant Rx1 containing amino acids 96 to 314.

Example 2
Competitive Inhibition of Anti-Rx1 Polyclonal Antibodies with the PspA Antigens of Different Strains Competitive inhibition of anti-PARx1 binding to PARx1 antigen was 15 analyzed using a BIAcore® sensor chip, coated with PARx1 antigen. The results are shown in FIG. 9. Rabbit polyclonal anti-PARx1 (1200 ng/ml) was allowed to react to the chip either alone, or in the presence of increasing concentration of PARx1 antigen (indicated by + in FIG. 9) or PA314 PspA antigen (indicated by squares in FIG. 9); the PA314 PspA antigen contains amino acids 96 to 314 of Rx1. The concentration of uninhibited antibody able to bind to the PARx1 antigen on the sensory chip surface was measured using mass transport measurements on the BIAcore® instrument. The mouse monoclonal IgG anti-PspA antibody, P81–122F10.A11 was used as a standard for these measurements.

The results of these experiments indicated that the N-terminal conserved region does not contain antigenic epitopes for the PspA response, and that the conserved region at the C-terminal end of the alpha helix contains cross-reactive and protective epitopes that are critical to the development of a broadly efficacious PspA vaccine. Further, FIG. 9 demonstrates the lack of relevance of the first 60 amino acids of the N-terminal region of the alpha helix, as the PA314 PspA antigen used in the competition assays above contains amino acids 96 to 314 of Rx1.

Figure 10:
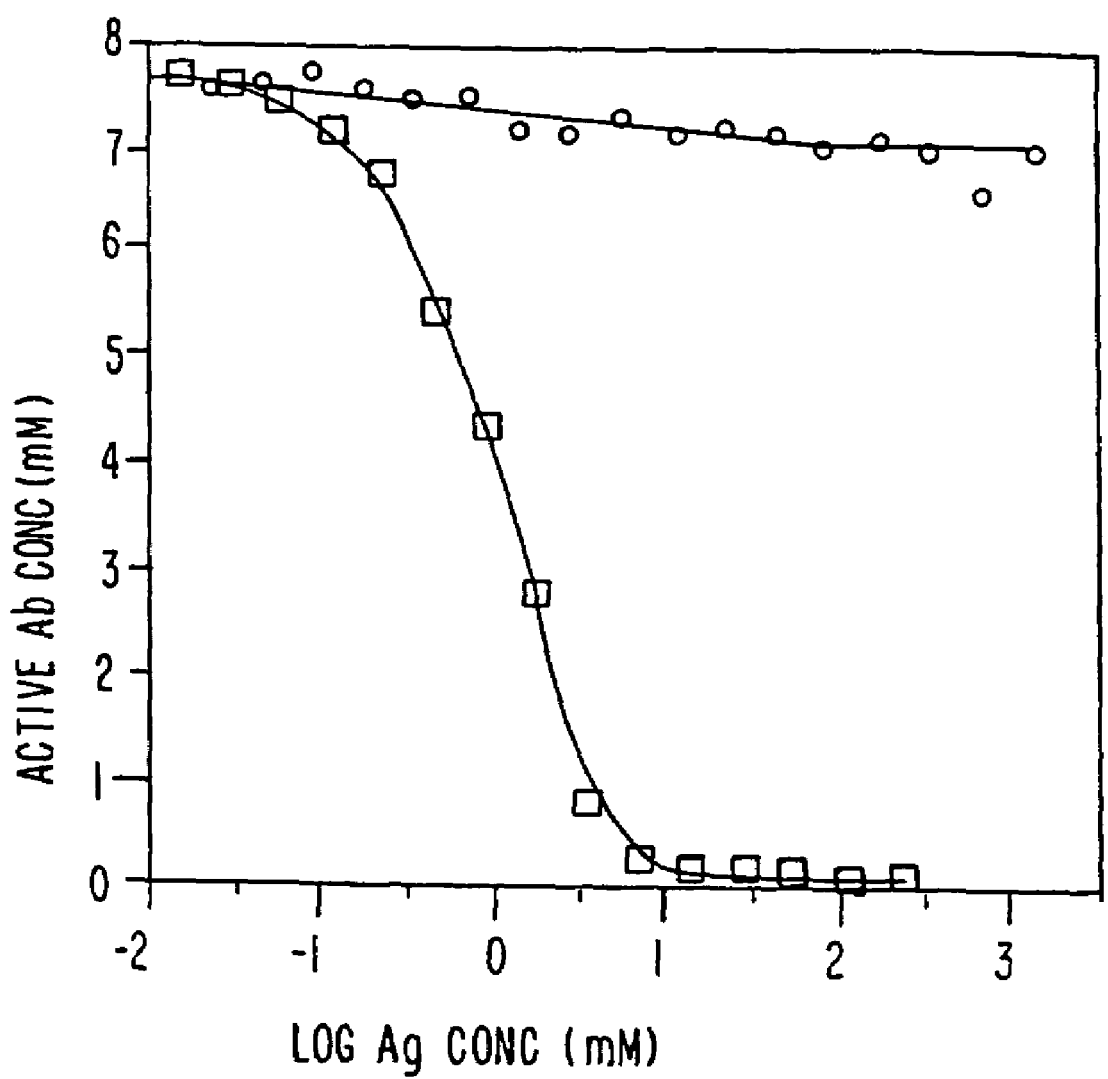
FIG. 10 shows the inhibition of polyclonal rabbit anti-Rx1 antibodies by PARx1 and PAEF5668 antigens.

FIG. 10 shows the inhibition of PARx1 and PAEF5668 antigens. A BIAcore® sensory chip was coated with PARx1 antigen and rabbit polyclonal anti-PARx1 (7 mM) was allowed to react to the chip either alone, or in the presence of increasing concentration of PARx1 antigen (represented by squares in FIG. 10) or PAEF5668 antigen (represented by circles in FIG. 10). The concentration (mM) of these competitive antigens is shown on the X axis on a logarithmic scale, while the concentration (mM) of uninhibited polyclonal antibody able to bind to the PARx1 antigen on the sensory chip was measured using mass transport measurements on the BIAcore® instrument, and is shown on the Y axis in FIG. 10.

As expected, the concentration of active, non-competitively inhibited polyclonal anti-PARx1 decreased as the concentrations of competitive inhibitor increased. PARx1 antigen completely inhibited the polyclonal antibodies at sufficient concentrations of antigens in excess. The PAEF5668 antigen has a maximal inhibition of 8.4%. The mouse monoclonal IgG anti-PspA antibody, P81–122F10.A11 was used as a standard for calculating the concentrations of active polyclonal antibody in this assay.

Figure 11:
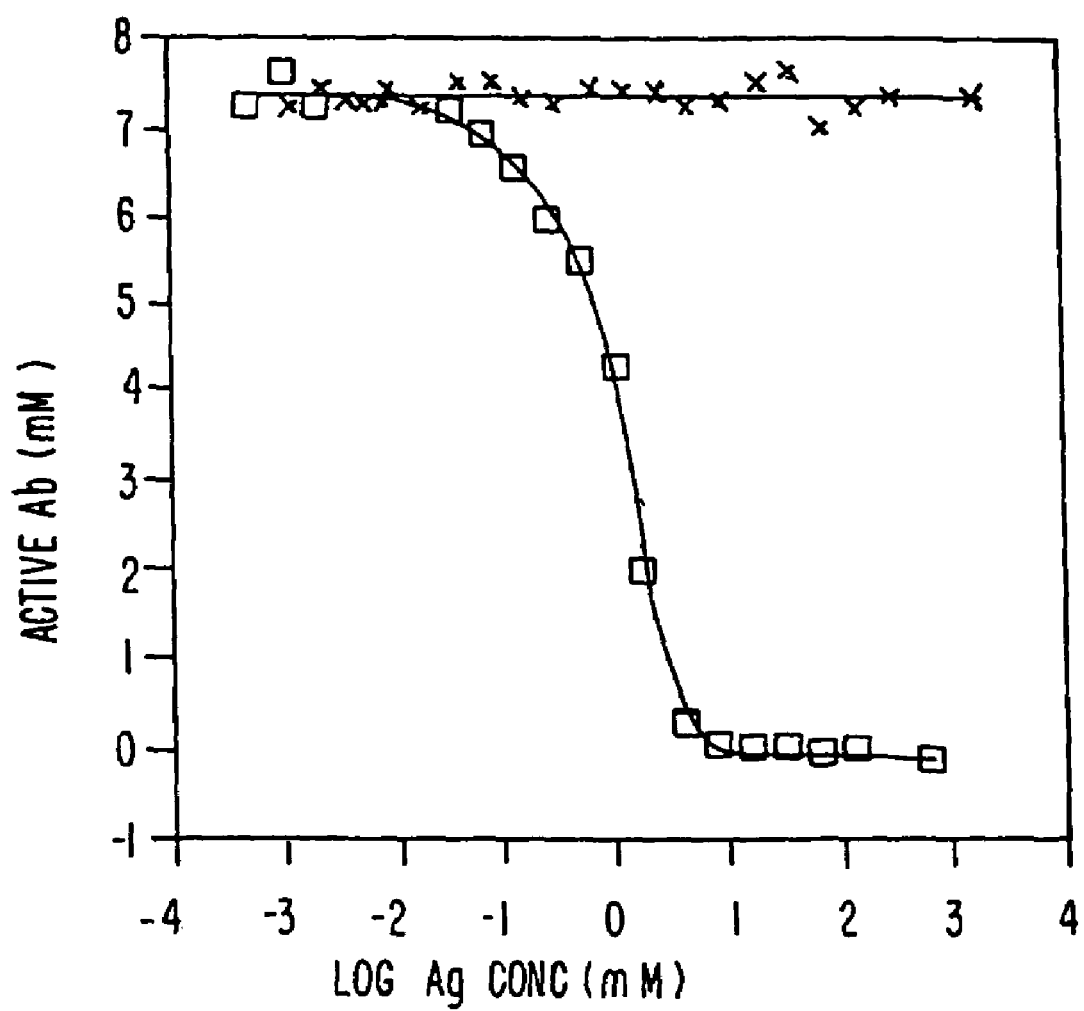
FIG. 11 shows the inhibition of polyclonal rabbit anti-Rx1 antibodies by PARx1 and PABG6380 antigens.

The results of the inhibition study by PARx1 and PABG6380 antigens is to shown in FIG. 11. A BIAcore® sensory chip was coated with PARx1 antigen and rabbit polyclonal anti-PARx1(7 mM) was allowed to react to the chip either alone, or in the presence of increasing concentration of PARx1 antigen (represented by squares in FIG. 11), or PABG6380 antigens (represented by X's in FIG. 11). The concentration (mM) of these competitive antigens is shown on the X axis on a logarithmic scale, while the concentration (mM) of uninhibited polyclonal antibody able to bind to the PARx1 antigen on the sensory chip was measured using mass transport measurements on the BIAcore® instrument, and is shown on the Y axis in FIG. 11.

As expected, the concentration of active, non-competitively inhibited polyclonal anti-PARx1 decreased as the concentration of competitive inhibitor increased. PARx1 antigen completely inhibited the polyclonal antibodies at sufficient concentrations of antigen in excess. The PABG6380 antigen did not significantly inhibit the polyclonal antibody reaction. The mouse monoclonal IgG anti-PspA antibody P81–122F10.A11 was used as a standard for calculating the concentrations of active polyclonal antibody in the assay.

Further, Table 8 shows the results of inhibition studies of polyclonal rabbit anti-Rx1 antibodies with representative strains of selective clades. As shown in the Table, anti-Rx1 antibodies inhibit clade 2 effectively, but the inhibition of PspAs in clades which differ from the specificity of the antibody itself is less effective.

TABLE 8

Inhibition of Polyclonal Rabbit anti-Rx1 Antibodies
(Inhibition of Anti-Clade 2 Antibody Reactivity)

| Clade | 1 | 2 | 2 | 2 | 4 | 6 | — |
|---|---|---|---|---|---|---|---|
| Strain | BG9739 | RX1 | R36A | WU2 | EF5668 | BG6380 | JY1119* |
| Antigen Name | BG9739/n | PARx1 | R36A/n | WU2/n | PAEF5668 | PABG6380 | JY1119/n |
| Antigen Type | native | recom.** | native | native | recom.** | recom.** | native |
| % Inhibition | 35.4 | 100.0 | 100.0 | 91.4 | 8.4 | 0.0 | 0.0 |

*JY1119 is an engineered PspA loss mutant and is used in this assay as a negative control
**recom. = recombinant Example 3

Competitive Inhibition of Clade Specific Anti-PspA Polyclonal Antibodies with PspA Antigens from Different Clades Rabbit polyclonal antiserum was raised against recombinantly expressed PspA antigens from representatives of the six clades. BG9739 was chosen as the representative of clade 1, Rx1 was the representative of clade 2, EF3296 was the representative of clade 3, EF5668 was the representative of clade 4, ATCC 6303 was the representative of clade 5 and BG6380 was the representative of clade 6.

Recombinant PspA antigens from each of the clades were each covalently linked to individual BIAcore sensory chips. Next, clade-specific polyclonal anti-PspA antibodies were allowed to react with each chip, either alone or in the presence of increasing concentration of each recombinant PspA antigen. The active concentration of anti-PspA antibodies that could bind to the PspA on the chip were determined using mass transport measurement. By comparing concentrations of the active antibody in uninhibited reactions and in reactions inhibited by the addition of soluble PspA strains was determined. These results are illustrated as estimated cross-reactivities in Table 9.

Cross-reactivity analyses were also performed using recombinant PspA antigens to coat BIAcore chips and the clade-specific polyclonal antisera described above, inhibited with native PspA antigens from representative clades. The results of the estimated cross-reactivities are shown in Table 10, and compare favorably to the results obtained with the results shown in Table 9. In each case, representatives of the same clade demonstrate the greatest cross-reactivity. Representatives of different clades within the same family demonstrate moderate cross-reactivity, and representatives of different families show the least cross-reactivity.

Example 4

Serotype Analysis of *S. pneumoniae* Strains by ELISA

Rabbit polyclonal antiserum was raised against recombinantly expressed PspA antigens from representatives of the six clades. BG739 was chosen as the representative of clade 1, Rx1 was the representative of clade 2, EF3296 was the representative of clade 3, EF5668 waste representative of clade 4, ATCC 6303 was the representative of clade 5 and BG6380 waste representative of clade 6.

Each of the antisera were first normalized to contain roughly equivalent specific activities. Then, sequential 1.5 fold dilutions of the antisera were reacted with ELISA plates coated with cetavalon lysates of representatives of each clade. As a negative control, the pspA gene of a *S. pneumoniae* strain was "knocked out", i.e., rendered inactive by a recombination event, and cetavalon lysates of this knock out strain were used to coat ELISA plate wells. Next, each well was incubated with goat anti-rabbit IgG-alkaline phosphatase conjugates (Kierkegaard and Perry, Gaithersburg, Md.) and washed, then p-Nitrophenyl Phosphate (Sigma Diagnostics, St. Louis) was added. Results of the calorimetric reactions were read at 405 nm.

Mixtures of antisera were prepared, combining equal specific activities of anti-Rx1, EF3296 and EF5668 in one cocktail, and anti-Rx1, EF3296, EF5668 and B06380 in a second cocktail. These cocktails contained antibodies which reacted with clades 2, 3 and 4 or 2, 3, 4 and 6 and were used to approximate the ability of various vaccine combinations to confer broad immunity. Mixtures of these antibodies reacted well with each of the *S. pneumoniae* strains tested, demonstrating that combinations of vaccines based on the clade definitions of the present invention should confer immunity against a broad range of *S. pneumoniae* isolates.

TABLE 9

| | | | | Cross-Reacting PspA Antigens | | | | | |
|---|---|---|---|---|---|---|---|---|---|
| | Family | | | 1 | 2 | 3 | | | 4 |
| | | Clade | | 1 | 2 | 3 | 4 | 5 | 6 |
| | | | Strain | BG9739 | Rx1 | EF3296 | EF5668 | ATC 6303 | BG6380 |
| Rabbit Anti-PspA Strain | 1 | 1 | BG9739 | 100 | 23 | 0 | 0 | 0 | 1 |
| | | 2 | Rx1 | 34 | 100 | 0 | 5 | 0 | 3 |
| | 2 | 3 | EF3296 | 0 | 0 | 100 | 0 | 0 | 2 |
| | | 3 | EF5668 | 4 | 5 | 10 | 100 | 67 | 1 |
| | | 5 | ATCC 6303 | 0 | 0 | 7 | 86 | 100 | 0 |
| | 4 | 6 | BG6380 | 0 | 0 | 4 | 0 | 0 | 100 |

Polyclonal antibodies to PspAs from individual clades demonstrated little cross-reactivity with representatives of other families. Significant cross-reactivity was observed between strains of clades 1 and 2 and between strains of clades 4 and 5. This observation is consistent with the grouping of these clades into families 1 and 3, respectively. Each strain could be serotyped and placed within a defined family or clade of PspA based on reactivity with polyclonal anti-PspA.

A total of 437 S. pneumoniae strains from the United States and Europe were evaluated by the polyclonal anti-PSA ELISA method. The results of this analysis are shown in Table 11.

TABLE 10

Percentage Cross Reactivity With Native PspA Antigens

| | | | Cross-Reacting PspA Antigens of Family/Clade | | | | | |
|---|---|---|---|---|---|---|---|---|
| Family | | | 1 | | 2 | 3 | | 4 |
| | | Clade | 1 | 2 | 3 | 4 | 5 | 6 |
| Rabbit Anti-PspA Clade | 1 | 1 | >91–86 | 33–16 | 3–0 | 24–4 | 0 | 8 |
| | | 2 | 52–25 | >85–50 | 3–0 | 12–8 | 4 | 3 |
| | 2 | 3 | 0 | 2–0 | >95–33 | 8–3 | 0 | 0 |
| | 3 | 4 | 3–0 | 15–9 | 22–9 | 100–70 | 72 | 3 |
| | | 5 | 13–3 | 6–0 | 11–0 | 81–48 | 100 | 10 |
| | 4 | 6 | 24–9 | 24–5 | 15–12 | 30–20 | 5 | >80 |

TABLE 11

| Source of Strains | Location | % of Strains of that Clade (# of Strains) | | | | | | | Total # of Strains |
|---|---|---|---|---|---|---|---|---|---|
| | | 1 | 2 | 3 | 4 | 5 | 6 | 0 | |
| CDC | U.S.A. | 9.2 (28) | 31.4 (96) | 25.8 (79) | 26.1 (80) | 2.3 (7) | 3.9 (12) | 1.3 (4) | 306 |
| PMC | ? | 7.1 (1) | 57.1 (8) | 14.3 (92) | 0 (0) | 0 (0) | 14.3 (2) | 7.1 (1) | 14 |
| UAB | U.S.A., Europe | 9.4 (11) | 47.0 (55) | 14.5 (17) | 18.8 (22) | 4.3 (5) | 3.4 (4) | 1.7 (2) | 117 |

Approximately 36% of all strains examined were serotyped as clade 2, 22% as clade 3 and 23% as clade 4. A vaccine comprised of PspAs from these three clades alone would cover greater than 80% of the S. pneumoniae strains examined (Table 11). Of the 437 strains examined, 98.4% of these strains could be serotyped into one of the six clades, again demonstrating the potential for a finite number of vaccine components, based on clade-specific PspAs, to confer broad immunity against infection caused by S. pneumoniae (Table 11). In fact, based on the high degree of cross-reactivity within families, a vaccine composition comprised of a single representative member of each family should confer such immunity.

Having thus described in detail certain preferred embodiments of the present invention, it is to be understood that the invention defined by the appended claims is not to be limited by particular details set forth in the above description, as many apparent variations thereof are possible without departing from the spirit or scope thereof.

REFERENCES

1. Center of Disease Control. 19484. Pneumococcal polysaccharide vaccine usage, United States, MMWR 33: 273–276, 281.

2. Mufson, M. A., G. Oley and D. Hughey, 1982. Pneumococcal disease in a medium-sized community in the United States. JAMA 248: 1486–1489.

3. Hook, E. W., C. A. Horton and D. R. Schaberg. 1983. Failure of intensive care unit support to influence mortality from pneumococcal bacteremia. JAMA 249: 1055–1057.

4. Breiman, R. F., J. S. Spika, V. J. Navarro, P. M. Darden and C. P. Darby. 1990. Pneumococcal bacteremia in Charleston County, S.C., Arch. Intern. Med. 150: 1401–1405.

5. Afessa, B., W. L. Greaves and W. R. Frederick. 1995. Pneumococcal bacterimia in adults: a 14-year experience in an inner-city university hospital. Clin. Infec. Diseases 21: 345–351.

6. Fang, G. D., M. Fine, J. Orloff, D. Arisumi, V. L. Yu, W. Kapoor, J. T., Grayston. S. P. Wang, R. Kohler, R. R. Muder and et al. 1990. New and emerging etiologies for community-acquired pneumonia with implications for therapy. A prospective multicenter study of 359 cases. Medicine (Baltimore) 69: 307–316.

7. Marrie, T. J., H. Durant and L. Yates. 1989. Community-acquired pneumonia requiring hospitalization: 5-year prospective study. Rev. Infect. Dis. 11: 586–599.

8. Torres, A., J. Serra-Batlles, A. Ferrer, P. Jimeniz, R. Celis, E. Cobo and R. Rodriquez-Roisin. 1991. Severe community-acquired pneumonia. Epidemiology and prognostic factors. Am Rev Respir Dis. 144:312–318.

9. Bluestone, C. D., J. S. Stephenson and L. M. Martin. 1992. Ten-year review of otitis media pathogens. Pediatr. Infect. Dis. J. 11: S7–11.

10. Teele, D. W., J. O. Klein, B. Rosner and G. B. O. M. S. Group. 1989. Epidemiology of otitis media during the first seven years of life of children in greater Boston: a prospective cohort study. J. Infect. Dis. 160: 83–94.

11. Schutze, G. E., S. L. Kaplan and R. F. Jacobs. 1994. Resistant pneumococcus: A worldwide problem. Infection 22: 233–237.

12. Privitera, G. 1994. Penicillin resistance among Streptococcus pneumoniae in Europe. Diagnostic Microbiology and Infectious Disease 19: 157–161.

13. Bizzozero, O. G. Jr. and V. T. Andriole. 1969. Tetracycline-resistant pneumococcal infection. Incidence, clinical presentation and laboratory evaluation. Arch Intern Med. 123: 388–393.

14. Workman, M. R., M. Layton, M. Hussein, J. Philpott-Howard and R. C. George. 1993. Nasal carriage of penicillin-resistant pneumococcus in sickle cell patients (letter). Lancet 342: 746–747.

15. Koornhof, H. J., A. Wasas and K. Klugman. 1992. Antimicrobial resistance in *Streptococcus pneumoniae*: a South African perspective. Clin. Infect. Dis. 15: 84–94.

16. Dagan, R., P. Yagupsky, A. Goldbart, A. Wasas and K. Klugman. 1994. Increasing prevalence of penicillin-resistant pneumococcal infections in children in southern Israel: implications for future immunization policies. Pediatr. Infect. Dis. J. 13: 782–786.

17. Reichler, M. R., J. Rakovsky, A. Sobotova, M. Slacikova, B. Hlavacova, B. Hill, L. Krajcikova, P. Tarina, R. R. Facklam and R. F. Breiman. 1995. Multiple antimicrobial resistance of pneumococci in children with otitis media, bacteremia, and meningitis in Slovakia. J. Infect. Dis. 171: 1491–1496.

18. Freidland, I. R., S. Shelton, M. Paris, S. Rinderknecht, S. Ehrett, K. Krisher, and G. H. McCracken, Jr., 1993. Dilemmas in diagnosis and management of cephalosporin-resistant *Streptococcus pneumoniae* meningitis. Pediatr. Infect. Dis. J. 12: 196–200.

19. Fedson, D. S., and D. M. Musher. 1994. Pneumococcal Vaccine. In Vaccines. S. A. Plotkin and J. E. A. Montimer, Eds. W. B. Saunders Co., Philadelphia, Pa., p. 517–564.

20. Takala, A. K., J. Eskola, M. Leinonen, H. Kayhty, A. Nissinen, E. Pekkanen and P. H. Makela. 1991. Reduction of oropharyngeal carriage of *Haemophilus influenzae* type b (Hib) in children immunized with an Hib conjugate vaccine. J. Infect. Dis. 164: 982–986.

21. Takala, A. K., M. Santosham, J. Almeido-Hill, M. Wolff, W. Newcomer, R. Reid, H. Kayhty, E. Esko and P. H. Makela. 1993. Vaccination with *Haemophilus influenzae* type b meningococcal protein conjugate vaccine reduces oropharyngeal carriage of *Haemophilus influenzae* type b among American Indian children. Pediatr. Infect. Dis. J. 12: 593–599.

22. Ward, J., J. M. Lieberman and S. L. Cochi. 1994. *Haemopbilus influenzae* vaccines. In Vaccines. S. A. Plotkin and J. E. A. Montimer, Eds. W. B. Saunders Co., Philadelphia, Pa., p. 337–386.

23. Murphy, T. V., P. Pastor, F. Medley, M. T. Osterholm, and D. M. Cranoff. 1993. Decreased Haemophilus colonization in children vaccinated with *Haemophilus influenzae* type b conjugate vaccine. J. Pediatr. 122: 517–523.

24. Mohle-Boetani, J. C., G. Ajello, E. Breneman, K. A., Deaver, C. Harvey, B. D. Plikaytis, M. M. Farley, D. S. Stephens and J. D. Wenger. 1993. Carriage of *Haemophilus influenzae* type b in children after widespread vaccination with conjugate *Haemophilus influenzae* type b vaccines. Pediatr. Infect. Dis. J. 12: 589–593.

25. Watson, D. A. and D. M. Musher. 1990. Interruption of capsule production in *Streptococcus pneumonia* serotype 3 by insertion of transposon Tn916. Infect. Immun. 58: 135–138.

26. Avery, O. T. and R. Dubos. 1931. The protective action of specific enzyme against type III pneumococcus infection in mice. J. Exp. Med. 54: 73–89.

27. Alonso DeVelasco, E., A. F. M. Verheul, J. Verhoef and H. Snippe. 1995. *Streptococcus pneumoniae*: virulence factors, pathogenesis and vaccines. Microbiological Reviews 59: 591–603.

28. Butler, J. C., R. F. Breiman, S. F. Campbell, H. B. Lipman, C. V. Broome and R. R. Facklam. 1993. Pneumococcal polysaccharide vaccine efficacy. An evaluation of current recommendations. JAMA 270: 1826–1831.

29. Hirschmann, J. V., and B. A. Lipsky. 1994. The pneumococcal vaccine after 15 years of use. Arch Intern Med. 154: 373–377.

30. Briles, D. E., J. Yother and L. S. McDaniel. 1988. Role of pneumococcal surface protein A in the virulence of *Streptococcus pneumoniae*. Rev. Infect. Dis. 10: S372–4.

31. Talkington, D. F., D. C. Voellinger, L. S. McDaniel and D. E. Briles. 1992. Analysis of pneumococcal PspA microheterogeneity in SDS-polyacrylaminde gels and the association of PspA with the cell membrane. Microb. Pathogen. 13: 343–355.

32. Yother, J. and D. E. Briles. 1992. Structural properties and evolutionary relationships of PspA, a surface protein of *Streptococcus pneumoniae*, as revealed by sequence analysis. J. Bacteriol. 174: 601–609.

33. Yother, J. and J. M. White. 1994. Novel surface attachment mechanism of the *Streptococcus pneumoniae* protein PspA. J. Bacteriol. 176: 2976–85.

34. McDaniel, L. S., B. A. Ralph, D. O. McDaniel and D. E. Briles. 1994. Localization of protection-eliciting epitopes of PspA of *Streptococcus pneumoniae* between amino acids residues 192 and 260. Microb. Pathog. 17: 323–337.

35. Ralph, B. A., D. E. Briles and L. S. McDaniel. 1994. Cross-reactive protection eliciting epitopes of pneumococcal surface protein A. Ann N Y Acad. Sci. 730: 361–3.

36. Waltman, W. D., L. S. McDaniel, B. Andersson, L. Bland, B. M. Gray, C. S. Eden and D. E. Briles. 1988. Protein serotyping of *Streptococcus pneumoniae* based on reactivity to six monoclonal antibodies. Microb. Pathog. 5: 159–67.

What is claimed:

1. A vaccine or immunogenic composition comprising at least an isolated PspA and an isolated immunogenic fragment of PspA from *S. pneumoniae* strains from at least two PspA families, wherein the isolated PspA is from one PspA family and the isolated immunogenic fragment of PspA is from another PspA family and the at least two families comprise one or more clades selected from the group consisting of clade 1, clade 2, clade 3, clade 4, clade 5, and clade 6.

2. The vaccine or immunogenic composition of claim 1, wherein the composition comprises an isolated PspA or an isolated immunogenic fragment of PspA from clade 1.

3. The vaccine or immunogenic composition of claim 2, wherein the composition comprises an isolated PspA or an isolated immunogenic fragment of PspA having an amino acid sequence of SEQ ID NO: 1.

4. The vaccine or immunogenic composition of claim 2, wherein the composition comprises an isolated PspA or an isolated immunogenic fragment of PspA from strain BG6692 having an amino acid sequence of SEQ ID NO: 2.

5. The vaccine or immunogenic composition of claim 2, wherein the composition comprises an isolated PspA or an isolated immunogenic fragment of PspA from strain BG8838 having an amino acid sequence of SEQ ID NO: 3.

6. The vaccine or immunogenic composition of claim 2, wherein the composition comprises an isolated PspA or an isolated immunogenic fragment of PspA from strain BG9739 having an amino acid sequence of SEQ ID NO: 4.

7. The vaccine or immunogenic composition of claim 2, wherein the composition comprises an isolated PspA or an isolated immunogenic fragment of PspA from strain DBL6A having an amino acid sequence of SEQ ID NO: 5.

8. The vaccine or immunogenic composition of claim 2, wherein the composition comprises an isolated PspA or an isolated immunogenic fragment of PspA from strain L81905 having an amino acid sequence of SEQ ID NO: 6.

9. The vaccine or immunogenic composition of claim 2, wherein the composition comprises an isolated PspA or an isolated immunogenic fragment of PspA from strain BG8743 having an amino acid sequence of SEQ ID NO: 7.

10. The vaccine or immunogenic composition of claim 2, wherein the composition comprises an isolated PspA or an isolated immunogenic fragment of PspA from strain DBL1 having an amino acid sequence of SEQ ID NO: 8.

11. The vaccine or immunogenic composition of claim 2, wherein the composition comprises an isolated PspA or an isolated immunogenic fragment of PspA from strain AC94 having an amino acid sequence of SEQ ID NO: 9.

12. The vaccine or immunogenic composition of claim 1, wherein the composition comprises an isolated PspA or an isolated immunogenic fragment of PspA from clade 2.

13. The vaccine or immunogenic composition of claim 12, wherein the composition comprises an isolated PspA or an isolated immunogenic fragment of PspA having an amino acid sequence of SEQ ID NO: 10.

14. The vaccine or immunogenic composition of claim 12, wherein the composition comprises an isolated PspA or an isolated immunogenic fragment of PspA from strain EF10197 having an amino acid sequence of SEQ ID NO: 11.

15. The vaccine or immunogenic composition of claim 12, wherein the composition comprises an isolated PspA or an isolated immunogenic fragment of PspA from strain WU2 having an amino acid sequence of SEQ ID NO: 13.

16. The vaccine or immunogenic composition of claim 12, wherein the composition comprises an isolated PspA or an isolated immunogenic fragment of PspA from strain DBL5 having an amino acid sequence of SEQ ID NO: 14.

17. The vaccine or immunogenic composition of claim 12, wherein the composition comprises an isolated PspA or an isolated immunogenic fragment of PspA from strain EF6796 having an amino acid sequence of SEQ ID NO: 15.

18. The vaccine or immunogenic composition of claim 12, wherein the composition comprises an isolated PspA or an isolated immunogenic fragment of PspA from strain 0922134 having an amino acid sequence of SEQ ID NO: 16.

19. The vaccine or immunogenic composition of claim 12, wherein the composition comprises an isolated PspA or an isolated immunogenic fragment of PspA from strain BG9163 having an amino acid sequence of SEQ ID NO: 17.

20. The vaccine or immunogenic composition of claim 1, wherein the composition comprises an isolated PspA or an isolated immunogenic fragment of PspA from clade 3.

21. The vaccine or immunogenic composition of claim 20, wherein the composition comprises an isolated PspA or an isolated immunogenic fragment of PspA having an amino acid sequence of SEQ ID NO: 18.

22. The vaccine or immunogenic composition of claim 20, wherein the composition comprises an isolated PspA or an isolated immunogenic fragment of PspA from strain AC122 having an amino acid sequence of SEQ ID NO: 19.

23. The vaccine or immunogenic composition of claim 20, wherein the composition comprises an isolated PspA or an isolated immunogenic fragment of PspA from strain EF3296 having an amino acid sequence of SEQ ID NO: 20.

24. The vaccine or immunogenic composition of claim 20, wherein the composition comprises an isolated PspA or an isolated immunogenic fragment of PspA from strain BG8090 having an amino acid sequence of SEQ ID NO: 21.

25. The vaccine or immunogenic composition of claim 1, wherein the composition comprises an isolated PspA or an isolated immunogenic fragment of PspA from clade 4.

26. The vaccine or immunogenic composition of claim 25, wherein the composition comprises an isolated PspA or an isolated immunogenic fragment of PspA having an amino acid sequence of SEQ ID NO: 22.

27. The vaccine or immunogenic composition of claim 25, wherein the composition comprises an isolated PspA or an isolated immunogenic fragment of PspA from strain BG11703 having an amino acid sequence of SEQ ID NO: 23.

28. The vaccine or immunogenic composition of claim 25, wherein the composition comprises an isolated PspA or an isolated immunogenic fragment of PspA from strain BG7817 having an amino acid sequence of SEQ ID NO: 24.

29. The vaccine or immunogenic composition of claim 25, wherein the composition comprises an isolated PspA or an isolated immunogenic fragment of PspA from strain EF5668 having an amino acid sequence of SEQ ID NO: 25.

30. The vaccine or immunogenic composition of claim 25, wherein the composition comprises an isolated PspA or an isolated immunogenic fragment of PspA from strain BG7561 having an amino acid sequence of SEQ ID NO: 26.

31. The vaccine or immunogenic composition of claim 1, wherein the composition comprises an isolated PspA or an isolated immunogenic fragment of PspA from clade 5.

32. The vaccine or immunogenic composition of claim 31, wherein the composition comprises an isolated PspA or an isolated immunogenic fragment of PspA from strain ATCC6303 having an amino acid sequence of SEQ ID NO: 27.

33. The vaccine or immunogenic composition of claim 1, wherein the composition comprises an isolated PspA or an isolated immunogenic fragment of PspA from clade 6.

34. The vaccine or immunogenic composition of claim 33, wherein the composition comprises an isolated PspA or an isolated immunogenic fragment of PspA from strain BG6380 having an amino acid sequence of SEQ ID NO: 28.

* * * * *

SEQUENCE LISTING

<160> NUMBER OF SEQ ID NOS: 28

<210> SEQ ID NO 1
<211> LENGTH: 98
<212> TYPE: PRT
<213> ORGANISM: Streptococcus pneumoniae

<400> SEQUENCE: 1

Leu Lys Glu Ile Asp Glu Ser Asp Ser Glu Asp Tyr Val Lys Glu Gly
1               5                   10                  15

Leu Arg Ala Pro Leu Gln Ser Glu Leu Asp Ala Lys Gln Ala Lys Leu
            20                  25                  30

```
Ser Lys Leu Glu Glu Leu Ser Asp Lys Ile Asp Glu Leu Asp Ala Glu
        35                  40                  45

Ile Ala Lys Leu Glu Lys Asp Val Glu Asp Phe Lys Asn Ser Asp Gly
    50                  55                  60

Glu Gln Ala Gln Tyr Leu Ala Ala Glu Glu Asp Leu Ala Lys Lys
65                  70                  75                  80

Ala Glu Leu Glu Lys Thr Glu Ala Asp Leu Lys Lys Ala Val His Glu
            85                  90                  95

Pro Glu

<210> SEQ ID NO 2
<211> LENGTH: 100
<212> TYPE: PRT
<213> ORGANISM: Streptococcus pneumoniae

<400> SEQUENCE: 2

Leu Lys Glu Ile Asp Glu Ser Asp Ser Glu Asp Tyr Val Lys Glu Gly
1               5                   10                  15

Leu Arg Ala Pro Leu Gln Ser Glu Leu Asp Ala Lys Gln Ala Lys Leu
            20                  25                  30

Ser Lys Leu Glu Glu Leu Ser Asp Lys Ile Asp Glu Leu Asp Ala Glu
        35                  40                  45

Ile Ala Lys Leu Glu Lys Asn Val Glu Asp Phe Lys Asn Ser Asn Gly
    50                  55                  60

Glu Gln Ala Glu Gln Tyr Arg Ala Ala Glu Glu Asp Leu Ala Ala
65                  70                  75                  80

Lys Gln Ala Glu Leu Glu Lys Thr Glu Ala Asp Leu Lys Lys Ala Val
            85                  90                  95

His Glu Pro Glu
            100

<210> SEQ ID NO 3
<211> LENGTH: 100
<212> TYPE: PRT
<213> ORGANISM: Streptococcus pneumoniae

<400> SEQUENCE: 3

Leu Lys Glu Ile Asp Glu Ser Asp Ser Glu Asp Tyr Val Lys Glu Gly
1               5                   10                  15

Leu Arg Ala Pro Leu Gln Ser Glu Leu Asp Ala Lys Gln Ala Lys Leu
            20                  25                  30

Ser Lys Leu Glu Glu Leu Ser Asp Lys Ile Asp Glu Leu Asp Ala Glu
        35                  40                  45

Ile Ala Lys Leu Glu Lys Asn Val Glu Asp Phe Lys Asn Ser Asn Gly
    50                  55                  60

Glu Glu Ala Glu Gln Tyr Arg Ala Ala Ala Gly Glu Asp Leu Ala Ala
65                  70                  75                  80

Lys Gln Ala Glu Leu Glu Lys Thr Glu Ala Asp Leu Lys Lys Ala Val
            85                  90                  95

His Glu Pro Glu
            100

<210> SEQ ID NO 4
<211> LENGTH: 100
<212> TYPE: PRT
<213> ORGANISM: Streptococcus pneumoniae
```

```
<400> SEQUENCE: 4

Leu Lys Glu Ile Asp Glu Ser Asp Ser Glu Asp Tyr Val Lys Glu Gly
1               5                   10                  15

Glu Arg Ala Pro Leu Gln Ser Glu Leu Asp Ala Lys Gln Ala Lys Leu
            20                  25                  30

Ser Lys Leu Glu Glu Leu Ser Asp Lys Ile Asp Glu Leu Asp Ala Glu
        35                  40                  45

Ile Ala Lys Leu Glu Lys Asp Val Glu Asp Phe Lys Asn Ser Asp Gly
    50                  55                  60

Glu Gln Ala Gly Gln Tyr Leu Ala Ala Ala Gly Glu Asp Leu Ile Ala
65                  70                  75                  80

Lys Lys Ala Glu Leu Glu Lys Ala Glu Ala Asp Leu Lys Lys Ala Val
                85                  90                  95

Asp Glu Pro Glu
            100

<210> SEQ ID NO 5
<211> LENGTH: 100
<212> TYPE: PRT
<213> ORGANISM: Streptococcus pneumoniae

<400> SEQUENCE: 5

Leu Lys Glu Ile Asp Glu Ser Asp Ser Glu Asp Tyr Val Lys Glu Gly
1               5                   10                  15

Glu Arg Ala Pro Leu Gln Ser Glu Leu Asp Ala Lys Gln Ala Lys Leu
            20                  25                  30

Ser Lys Leu Glu Glu Leu Ser Asp Lys Ile Asp Glu Leu Asp Ala Glu
        35                  40                  45

Ile Ala Lys Leu Glu Lys Asp Val Glu Asp Phe Lys Asn Ser Asp Gly
    50                  55                  60

Glu Gln Ala Gly Gln Tyr Leu Ala Ala Ala Glu Glu Asp Leu Ile Ala
65                  70                  75                  80

Lys Lys Ala Glu Leu Glu Gln Thr Glu Ala Asp Leu Lys Lys Ala Val
                85                  90                  95

His Glu Pro Glu
            100

<210> SEQ ID NO 6
<211> LENGTH: 100
<212> TYPE: PRT
<213> ORGANISM: Streptococcus pneumoniae
<220> FEATURE:
<221> NAME/KEY: UNSURE
<222> LOCATION: (1)..(100)
<223> OTHER INFORMATION: amino acid 'Xaa' can be any amino acid

<400> SEQUENCE: 6

Leu Lys Glu Ile Asp Glu Ser Asp Ser Glu Asp Tyr Val Lys Glu Gly
1               5                   10                  15

Glu Arg Ala Pro Leu Gln Ser Glu Leu Asp Ala Lys Gln Ala Lys Leu
            20                  25                  30

Ser Lys Leu Glu Glu Xaa Ser Asp Lys Xaa Asp Glu Leu Asp Ala Glu
        35                  40                  45

Ile Ala Lys Leu Glu Lys Asp Val Glu Asp Phe Lys Asn Ser Asp Gly
    50                  55                  60

Glu Gln Ala Gly Gln Tyr Leu Ala Ala Ala Glu Glu Asp Leu Ile Ala
65                  70                  75                  80
```

```
Lys Lys Ala Xaa Leu Glu Lys Ala Glu Ala Asp Leu Lys Lys Ala Val
                85                  90                  95

Asp Glu Pro Glu
            100

<210> SEQ ID NO 7
<211> LENGTH: 100
<212> TYPE: PRT
<213> ORGANISM: Streptococcus pneumoniae
<220> FEATURE:
<221> NAME/KEY: UNSURE
<222> LOCATION: (1)..(100)
<223> OTHER INFORMATION: amino acid 'Xaa' can be any amino acid

<400> SEQUENCE: 7

Leu Lys Glu Ile Asp Glu Ser Asp Ser Glu Asp Tyr Glu Lys Glu Gly
1               5                   10                  15

Leu Arg Ala Pro Leu Gln Ser Lys Leu Asp Ala Lys Lys Ala Lys Leu
                20                  25                  30

Ser Lys Leu Asp Glu Xaa Ser Asp Lys Xaa Asp Glu Leu Asp Ala Glu
                35                  40                  45

Ile Ala Lys Leu Glu Lys Asp Val Gly Asp Phe Pro Asn Ser Asp Gly
            50                  55                  60

Glu Gln Ala Gly Gln Tyr Leu Val Ala Ala Glu Lys Asp Leu Asp Ala
65                  70                  75                  80

Lys Glu Ala Glu Leu Gly Asn Thr Gly Ala Asp Leu Lys Lys Ala Val
                85                  90                  95

Asp Glu Pro Glu
            100

<210> SEQ ID NO 8
<211> LENGTH: 100
<212> TYPE: PRT
<213> ORGANISM: Streptococcus pneumoniae

<400> SEQUENCE: 8

Leu Lys Gly Ile Asp Glu Ser Asp Ser Glu Asp Tyr Val Lys Glu Gly
1               5                   10                  15

Leu Arg Ala Pro Leu Gln Ser Glu Leu Asp Ala Lys Arg Thr Lys Leu
                20                  25                  30

Ser Thr Leu Glu Glu Leu Ser Asp Lys Ile Asp Glu Leu Asp Ala Glu
                35                  40                  45

Ile Pro Lys Leu Glu Lys Asn Val Glu Tyr Phe Lys Leu Thr Asp Ala
            50                  55                  60

Glu Gln Thr Glu Gln Tyr Leu Ala Ala Ala Glu Lys Asp Leu Ala Asp
65                  70                  75                  80

Lys Lys Ala Glu Leu Glu Lys Thr Glu Ala Asp Leu Lys Lys Ala Val
                85                  90                  95

His Glu Pro Glu
            100

<210> SEQ ID NO 9
<211> LENGTH: 101
<212> TYPE: PRT
<213> ORGANISM: Streptococcus pneumoniae

<400> SEQUENCE: 9

Leu Lys Glu Ile Asp Glu Ser Asp Ser Glu Asp Tyr Val Lys Glu Gly
1               5                   10                  15
```

```
Leu Arg Val Pro Leu Gln Ser Glu Leu Asp Val Lys Gln Ala Lys Leu
            20                  25                  30

Leu Lys Leu Glu Glu Leu Ser Asp Lys Ile Asp Glu Leu Asp Ala Glu
        35                  40                  45

Ile Ala Lys Asn Leu Lys Lys Asp Val Glu Asp Phe Gln Asn Ser Gly
 50                  55                  60

Gly Gly Tyr Ser Ala Leu Tyr Leu Glu Ala Ala Glu Lys Asp Leu Val
 65                  70                  75                  80

Ala Lys Lys Ala Glu Leu Glu Lys Thr Glu Ala Asp Leu Lys Lys Ala
            85                  90                  95

Val His Glu Pro Glu
            100

<210> SEQ ID NO 10
<211> LENGTH: 100
<212> TYPE: PRT
<213> ORGANISM: Streptococcus pneumoniae

<400> SEQUENCE: 10

Leu Lys Glu Ile Asp Glu Ser Asp Ser Glu Asp Tyr Ala Lys Glu Gly
 1               5                  10                  15

Phe Arg Ala Pro Leu Gln Ser Lys Leu Asp Ala Lys Lys Ala Lys Leu
            20                  25                  30

Ser Lys Leu Glu Glu Leu Ser Asp Lys Ile Asp Glu Leu Asp Ala Glu
        35                  40                  45

Ile Ala Lys Leu Glu Cys Val Gln Leu Lys Asp Ala Glu Gly Asn Asn
 50                  55                  60

Asn Val Glu Ala Tyr Phe Lys Glu Gly Leu Glu Lys Thr Thr Ala Glu
 65                  70                  75                  80

Lys Lys Ala Glu Leu Glu Lys Ala Glu Ala Asp Leu Lys Lys Ala Val
            85                  90                  95

Asp Glu Pro Glu
            100

<210> SEQ ID NO 11
<211> LENGTH: 99
<212> TYPE: PRT
<213> ORGANISM: Streptococcus pneumoniae

<400> SEQUENCE: 11

Leu Lys Glu Ile Asp Glu Ser Asp Ser Glu Asp Tyr Val Lys Glu Gly
 1               5                  10                  15

Phe Arg Ala Pro Leu Gln Ser Glu Leu Asp Ala Lys Gln Ala Lys Leu
            20                  25                  30

Ser Lys Leu Glu Glu Leu Ser Asp Lys Ile Asp Glu Leu Asp Ala Glu
        35                  40                  45

Ile Ala Lys Leu Glu Asp Gln Leu Lys Ala Ala Glu Glu Asn Asn Asn
 50                  55                  60

Val Glu Asp Tyr Phe Lys Glu Gly Leu Glu Lys Thr Ile Ala Ala Lys
 65                  70                  75                  80

Lys Ala Glu Leu Glu Lys Thr Glu Ala Asp Leu Lys Lys Ala Val Asn
            85                  90                  95

Glu Pro Glu

<210> SEQ ID NO 12
<211> LENGTH: 100
<212> TYPE: PRT
```

<213> ORGANISM: Streptococcus pneumoniae

<400> SEQUENCE: 12

Leu Lys Glu Ile Asp Glu Ser Glu Ser Glu Asp Tyr Ala Lys Glu Gly
1               5                   10                  15

Phe Arg Ala Pro Leu Gln Ser Lys Leu Asp Ala Lys Gln Ala Lys Leu
            20                  25                  30

Ser Lys Leu Glu Glu Leu Ser Asp Lys Ile Asp Glu Leu Asp Ala Glu
        35                  40                  45

Ile Ala Lys Leu Glu Asp Gln Leu Lys Ala Ala Glu Glu Asn Asn
    50                  55                  60

Asn Val Glu Asp Tyr Phe Lys Glu Gly Leu Glu Lys Thr Ile Ala Ala
65                  70                  75                  80

Lys Lys Ala Glu Leu Glu Lys Thr Glu Ala Asp Leu Lys Lys Ala Val
                85                  90                  95

Asn Glu Pro Glu
            100

<210> SEQ ID NO 13
<211> LENGTH: 99
<212> TYPE: PRT
<213> ORGANISM: Streptococcus pneumoniae

<400> SEQUENCE: 13

Leu Lys Glu Ile Asp Glu Ser Glu Ser Glu Asp Tyr Ala Lys Glu Gly
1               5                   10                  15

Phe Arg Ala Pro Leu His Ser Lys Leu Asp Ala Lys Gln Ala Lys Leu
            20                  25                  30

Ser Lys Leu Glu Glu Leu Ser Asp Lys Ile Asp Glu Leu Asp Ala Glu
        35                  40                  45

Ile Ala Lys Leu Glu Asp Gln Leu Lys Ala Val Glu Glu Asn Asn Asn
    50                  55                  60

Val Glu Asp Tyr Ser Thr Glu Gly Leu Glu Lys Thr Ile Ala Ala Lys
65                  70                  75                  80

Lys Thr Glu Leu Glu Lys Thr Glu Ala Asp Leu Lys Lys Ala Val Asn
                85                  90                  95

Glu Pro Glu

<210> SEQ ID NO 14
<211> LENGTH: 99
<212> TYPE: PRT
<213> ORGANISM: Streptococcus pneumoniae
<220> FEATURE:
<221> NAME/KEY: UNSURE
<222> LOCATION: (1)..(99)
<223> OTHER INFORMATION: amino acid 'Xaa' can be any amino acid

<400> SEQUENCE: 14

Leu Lys Asp Ile Asp Glu Ser Asp Ser Glu Asp Tyr Ala Lys Glu Gly
1               5                   10                  15

Glu Arg Ala Pro Leu Gln Ser Glu Leu Asp Thr Lys Lys Ala Lys Leu
            20                  25                  30

Leu Lys Leu Glu Glu Leu Ser Gly Lys Ile Glu Glu Leu Asp Ala Glu
        35                  40                  45

Ile Xaa Glu Leu Glu Val Gln Leu Lys Asp Ala Glu Gly Asn Asn Asn
    50                  55                  60

Val Glu Ala Tyr Phe Lys Glu Gly Leu Glu Lys Thr Thr Ala Glu Lys
65                  70                  75                  80

```
Lys Ala Glu Leu Glu Lys Ala Glu Ala Asp Leu Lys Lys Ala Val Asp
                85                  90                  95

Glu Pro Glu

<210> SEQ ID NO 15
<211> LENGTH: 99
<212> TYPE: PRT
<213> ORGANISM: Streptococcus pneumoniae

<400> SEQUENCE: 15

Leu Glu Glu Ile Asn Glu Ser Asp Ser Glu Asp Tyr Ala Lys Glu Gly
1               5                   10                  15

Phe Arg Ala Pro Leu Gln Ser Lys Leu Asp Ala Lys Lys Ala Lys Leu
                20                  25                  30

Leu Lys Leu Glu Glu Leu Ser Gly Lys Ile Glu Glu Leu Asp Ala Glu
            35                  40                  45

Ile Ala Glu Leu Glu Val Gln Leu Lys Asp Ala Glu Gly Asn Asn Asn
    50                  55                  60

Val Glu Ala Tyr Phe Lys Glu Gly Leu Glu Lys Thr Thr Ala Glu Lys
65                  70                  75                  80

Lys Ala Glu Leu Glu Lys Ala Glu Ala Asp Leu Lys Lys Ala Val Asp
                85                  90                  95

Glu Pro Glu

<210> SEQ ID NO 16
<211> LENGTH: 99
<212> TYPE: PRT
<213> ORGANISM: Streptococcus pneumoniae

<400> SEQUENCE: 16

Leu Lys Glu Ile Asp Glu Ser Asp Ser Glu Asp Tyr Leu Lys Glu Gly
1               5                   10                  15

Glu Arg Ala Pro Leu Gln Ser Lys Leu Asp Thr Lys Lys Ala Lys Leu
                20                  25                  30

Ser Lys Leu Glu Glu Leu Ser Asp Lys Ile Asp Glu Leu Asp Ala Glu
            35                  40                  45

Ile Ala Lys Leu Glu Val Gln Leu Lys Asp Ala Glu Gly Asn Asn Asn
    50                  55                  60

Val Glu Ala Tyr Phe Lys Glu Gly Leu Glu Lys Thr Thr Ala Glu Lys
65                  70                  75                  80

Lys Ala Glu Leu Glu Lys Ala Glu Ala Asp Leu Lys Lys Ala Val Asp
                85                  90                  95

Glu Pro Glu

<210> SEQ ID NO 17
<211> LENGTH: 99
<212> TYPE: PRT
<213> ORGANISM: Streptococcus pneumoniae
<220> FEATURE:
<221> NAME/KEY: UNSURE
<222> LOCATION: (1)..(99)
<223> OTHER INFORMATION: amino acid 'Xaa' can be any amino acid

<400> SEQUENCE: 17

Pro Lys Arg Ile Met Ser Leu Ser Gln Lys Val Xaa Leu Lys Xaa Val
1               5                   10                  15

Cys Arg Ala Pro Leu Gln Ser Lys Leu Asp Ala Gln Lys Ala Glu Leu
                20                  25                  30
```

Leu Lys Leu Glu Glu Leu Ser Gly Lys Ile Lys Glu Leu Asp Ala Glu
            35                  40                  45

Ile Ala Glu Leu Glu Val Gln Leu Lys Asp Ala Glu Gly Asn Asn Asn
        50                  55                  60

Val Glu Ala Tyr Phe Lys Gly Leu Glu Lys Thr Thr Ala Glu Lys
65                  70                  75                  80

Lys Ala Glu Leu Glu Xaa Ala Xaa Ala Asp Leu Lys Lys Ala Val Asp
                85                  90                  95

Glu Pro Glu

<210> SEQ ID NO 18
<211> LENGTH: 102
<212> TYPE: PRT
<213> ORGANISM: Streptococcus pneumoniae

<400> SEQUENCE: 18

Leu Ala Lys Lys Gln Thr Glu Leu Glu Lys Leu Leu Asp Leu Asp Pro
1               5                   10                  15

Glu Gly Lys Thr Gln Asp Glu Leu Asp Lys Glu Ala Glu Ala Glu Leu
            20                  25                  30

Asp Lys Lys Ala Asp Glu Leu Pro Asn Lys Val Ala Asp Leu Glu Lys
        35                  40                  45

Glu Ile Ser Asn Leu Glu Ile Leu Leu Gly Gly Ala Asp Ser Glu Asp
    50                  55                  60

Asp Thr Ala Ala Leu Pro Asn Lys Leu Ala Thr Lys Lys Ala Glu Leu
65                  70                  75                  80

Glu Lys Thr Gln Lys Glu Leu Asp Ala Ala Leu Asn Glu Leu Gly Pro
                85                  90                  95

Asp Gly Asp Glu Glu Glu
            100

<210> SEQ ID NO 19
<211> LENGTH: 80
<212> TYPE: PRT
<213> ORGANISM: Streptococcus pneumoniae

<400> SEQUENCE: 19

Leu Asp Lys Glu Ala Gly Glu Ala Glu Leu Asp Lys Lys Ala Asp Gly
1               5                   10                  15

Leu Pro Asn Lys Val Ser Asp Leu Glu Lys Glu Ile Ser Asn Leu Glu
            20                  25                  30

Ile Leu Leu Gly Gly Ala Asp Ser Glu Asp Thr Ala Ala Leu Pro
        35                  40                  45

Asn Lys Leu Ala Thr Lys Lys Ala Glu Leu Glu Lys Thr Gln Lys Glu
    50                  55                  60

Leu Asp Ala Ala Leu Asn Glu Leu Gly Pro Asp Gly Asp Glu Glu Glu
65                  70                  75                  80

<210> SEQ ID NO 20
<211> LENGTH: 104
<212> TYPE: PRT
<213> ORGANISM: Streptococcus pneumoniae

<400> SEQUENCE: 20

Leu Ala Lys Lys Gln Thr Glu Leu Glu Lys Leu Leu Asp Ser Leu Asp
1               5                   10                  15

Pro Glu Gly Lys Thr Gln Asp Glu Leu Asp Lys Glu Ala Glu Glu Ala

```
                20              25              30
Glu Leu Asp Lys Lys Ala Asp Glu Leu Pro Asn Lys Val Ala Asp Leu
            35                  40                  45
Glu Lys Glu Ile Ser Asn Leu Glu Ile Leu Leu Gly Gly Ala Asp Ser
 50                  55                  60
Glu Asp Asp Thr Ala Ala Leu Pro Asn Lys Leu Ala Thr Lys Lys Ala
 65                  70                  75                  80
Glu Leu Glu Lys Thr Gln Lys Glu Leu Asp Ala Ala Leu Asn Glu Leu
                85                  90                  95
Gly Pro Asp Gly Asp Glu Glu Glu
            100

<210> SEQ ID NO 21
<211> LENGTH: 104
<212> TYPE: PRT
<213> ORGANISM: Streptococcus pneumoniae

<400> SEQUENCE: 21

Leu Ala Lys Lys Gln Thr Glu Leu Glu Lys Leu Leu Asp Asn Leu Asp
 1                   5                  10                  15
Pro Glu Gly Lys Thr Gln Asp Glu Leu Asp Lys Glu Ala Ala Glu Ala
                20                  25                  30
Glu Leu Asp Lys Lys Ala Asp Glu Leu Pro Asn Lys Val Ala Asp Leu
            35                  40                  45
Glu Lys Glu Ile Ser Asn Leu Glu Ile Leu Leu Gly Gly Ala Asp Pro
 50                  55                  60
Glu Asp Asp Thr Ala Ala Leu Pro Asn Lys Leu Ala Thr Lys Lys Ala
 65                  70                  75                  80
Glu Leu Glu Lys Thr Gln Lys Glu Leu Asp Ala Ala Leu Asn Glu Leu
                85                  90                  95
Gly Pro Asp Gly Asp Glu Glu Glu
            100

<210> SEQ ID NO 22
<211> LENGTH: 106
<212> TYPE: PRT
<213> ORGANISM: Streptococcus pneumoniae

<400> SEQUENCE: 22

Leu Glu Lys Ala Glu Ala Glu Leu Glu Asn Leu Leu Ser Thr Leu Asp
 1                   5                  10                  15
Pro Glu Gly Lys Thr Gln Asp Glu Leu Asp Lys Glu Ala Ala Glu Ala
                20                  25                  30
Glu Leu Asn Lys Lys Val Glu Ala Leu Pro Asn Gln Val Glu Leu Glu
            35                  40                  45
Glu Glu Leu Ser Lys Leu Glu Asp Asn Leu Lys Asp Ala Glu Thr Asn
 50                  55                  60
Val Glu Asp Tyr Ile Lys Gly Leu Glu Glu Ala Ile Ala Thr Lys
 65                  70                  75                  80
Gln Ala Glu Leu Glu Lys Thr Pro Lys Glu Leu Asp Ala Ala Leu Asn
                85                  90                  95
Glu Leu Gly Pro Asp Gly Asp Glu Glu Glu
            100                 105

<210> SEQ ID NO 23
<211> LENGTH: 108
<212> TYPE: PRT
```

<213> ORGANISM: Streptococcus pneumoniae

<400> SEQUENCE: 23

| Leu | Glu | Lys | Ala | Glu | Ala | Glu | Leu | Glu | Asn | Leu | Leu | Ser | Thr | Leu | Asp |
|---|---|---|---|---|---|---|---|---|---|---|---|---|---|---|---|
| 1 | | | | 5 | | | | | 10 | | | | | 15 | |

| Pro | Glu | Gly | Lys | Thr | Gln | Asp | Glu | Leu | Asp | Lys | Glu | Ala | Ala | Glu | Ala |
|---|---|---|---|---|---|---|---|---|---|---|---|---|---|---|---|
| | | | 20 | | | | | 25 | | | | | 30 | | |

| Glu | Leu | Asn | Lys | Lys | Val | Glu | Ala | Leu | Pro | Asn | Gln | Val | Ser | Glu | Leu |
|---|---|---|---|---|---|---|---|---|---|---|---|---|---|---|---|
| | | 35 | | | | | 40 | | | | | 45 | | | |

| Glu | Glu | Glu | Leu | Ser | Lys | Leu | Glu | Asp | Asn | Leu | Lys | Asp | Ala | Glu | Thr |
|---|---|---|---|---|---|---|---|---|---|---|---|---|---|---|---|
| | 50 | | | | | 55 | | | | | 60 | | | | |

| Asn | Asn | Val | Glu | Asp | Tyr | Ile | Lys | Glu | Gly | Leu | Glu | Ala | Ile | Ala |
|---|---|---|---|---|---|---|---|---|---|---|---|---|---|---|
| 65 | | | | 70 | | | | | 75 | | | | | 80 |

| Thr | Lys | Gln | Ala | Glu | Leu | Glu | Lys | Thr | Pro | Lys | Glu | Leu | Asp | Ala | Ala |
|---|---|---|---|---|---|---|---|---|---|---|---|---|---|---|---|
| | | | | 85 | | | | | 90 | | | | | 95 | |

| Leu | Asn | Glu | Leu | Gly | Pro | Asp | Gly | Asp | Glu | Glu | Glu |
|---|---|---|---|---|---|---|---|---|---|---|---|
| | | | 100 | | | | | 105 | | | |

<210> SEQ ID NO 24
<211> LENGTH: 108
<212> TYPE: PRT
<213> ORGANISM: Streptococcus pneumoniae

<400> SEQUENCE: 24

| Leu | Glu | Lys | Ala | Gly | Ala | Gly | Leu | Glu | Asn | Leu | Leu | Ser | Thr | Leu | Asp |
|---|---|---|---|---|---|---|---|---|---|---|---|---|---|---|---|
| 1 | | | | 5 | | | | | 10 | | | | | 15 | |

| Pro | Glu | Gly | Lys | Thr | Gln | Asp | Glu | Leu | Asp | Lys | Glu | Ala | Ala | Glu | Ala |
|---|---|---|---|---|---|---|---|---|---|---|---|---|---|---|---|
| | | | 20 | | | | | 25 | | | | | 30 | | |

| Glu | Leu | Asn | Lys | Lys | Val | Glu | Ala | Leu | Pro | Asn | Gln | Val | Ala | Glu | Leu |
|---|---|---|---|---|---|---|---|---|---|---|---|---|---|---|---|
| | | 35 | | | | | 40 | | | | | 45 | | | |

| Glu | Glu | Glu | Leu | Ser | Lys | Leu | Glu | Asp | Asn | Leu | Lys | Asp | Ala | Glu | Thr |
|---|---|---|---|---|---|---|---|---|---|---|---|---|---|---|---|
| | 50 | | | | | 55 | | | | | 60 | | | | |

| Asn | His | Val | Glu | Asp | Tyr | Ile | Lys | Glu | Gly | Leu | Glu | Ala | Ile | Ala |
|---|---|---|---|---|---|---|---|---|---|---|---|---|---|---|
| 65 | | | | 70 | | | | | 75 | | | | | 80 |

| Thr | Lys | Gln | Ala | Glu | Leu | Glu | Lys | Thr | Pro | Lys | Glu | Leu | Asp | Ala | Ala |
|---|---|---|---|---|---|---|---|---|---|---|---|---|---|---|---|
| | | | | 85 | | | | | 90 | | | | | 95 | |

| Leu | Asn | Glu | Leu | Gly | Pro | Asp | Gly | Asp | Glu | Glu | Glu |
|---|---|---|---|---|---|---|---|---|---|---|---|
| | | | 100 | | | | | 105 | | | |

<210> SEQ ID NO 25
<211> LENGTH: 108
<212> TYPE: PRT
<213> ORGANISM: Streptococcus pneumoniae

<400> SEQUENCE: 25

| Leu | Glu | Asp | Ala | Glu | Leu | Glu | Leu | Glu | Lys | Val | Leu | Ala | Thr | Leu | Asp |
|---|---|---|---|---|---|---|---|---|---|---|---|---|---|---|---|
| 1 | | | | 5 | | | | | 10 | | | | | 15 | |

| Pro | Glu | Gly | Lys | Thr | Gln | Asp | Glu | Leu | Asp | Lys | Glu | Ala | Ala | Glu | Ala |
|---|---|---|---|---|---|---|---|---|---|---|---|---|---|---|---|
| | | | 20 | | | | | 25 | | | | | 30 | | |

| Glu | Leu | Asn | Glu | Lys | Val | Glu | Ala | Leu | Gln | Asn | Gln | Val | Ala | Glu | Leu |
|---|---|---|---|---|---|---|---|---|---|---|---|---|---|---|---|
| | | 35 | | | | | 40 | | | | | 45 | | | |

| Glu | Glu | Glu | Leu | Ser | Lys | Leu | Glu | Asp | Asn | Leu | Lys | Asp | Ala | Glu | Thr |
|---|---|---|---|---|---|---|---|---|---|---|---|---|---|---|---|
| | 50 | | | | | 55 | | | | | 60 | | | | |

| Asn | Asn | Val | Glu | Asp | Tyr | Ile | Lys | Glu | Gly | Leu | Glu | Ala | Ile | Ala |
|---|---|---|---|---|---|---|---|---|---|---|---|---|---|---|
| 65 | | | | 70 | | | | | 75 | | | | | 80 |

| Thr | Lys | Lys | Ala | Glu | Leu | Glu | Lys | Thr | Gln | Lys | Glu | Leu | Asp | Ala | Ala |
|---|---|---|---|---|---|---|---|---|---|---|---|---|---|---|---|
| | | | | 85 | | | | | 90 | | | | | 95 | |

Leu Asn Glu Leu Gly Pro Asp Gly Asp Glu Glu Glu
            100                 105

<210> SEQ ID NO 26
<211> LENGTH: 108
<212> TYPE: PRT
<213> ORGANISM: Streptococcus pneumoniae
<220> FEATURE:
<221> NAME/KEY: UNSURE
<222> LOCATION: (1)..(108)
<223> OTHER INFORMATION: amino acid 'Xaa' can be any amino acid

<400> SEQUENCE: 26

Leu Glu Lys Ala Glu Ala Glu Leu Glu Asn Leu Leu Ser Thr Leu Asp
1               5                   10                  15

Pro Gly Gly Lys Thr Gln Asp Glu Leu Asp Lys Gly Ala Ala Glu Ala
            20                  25                  30

Glu Leu Asn Lys Lys Val Glu Ala Leu Pro Asn Pro Val Xaa Glu Leu
        35                  40                  45

Glu Glu Glu Leu Ser Pro Pro Glu Asp Asn Leu Lys Asp Ala Glu Thr
    50                  55                  60

Asn His Val Glu Asp Tyr Ile Lys Glu Gly Leu Glu Ala Ile Ala
65                  70                  75                  80

Thr Lys Gln Ala Glu Leu Glu Thr Pro Gln Glu Val Asp Ala Ala
                85                  90                  95

Leu Asn Asp Leu Val Pro Asp Gly Gly Glu Glu Glu
            100                 105

<210> SEQ ID NO 27
<211> LENGTH: 119
<212> TYPE: PRT
<213> ORGANISM: Streptococcus pneumoniae

<400> SEQUENCE: 27

Leu Glu Asp Ser Gly Leu Gly Leu Glu Lys Val Leu Ala Thr Leu Asp
1               5                   10                  15

Pro Gly Gly Glu Thr Pro Asp Gly Leu Asp Lys Glu Ala Ser Glu Asp
            20                  25                  30

Ser Asn Ile Gly Ala Leu Pro Asn Gln Val Ser Asp Leu Glu Asn Gln
        35                  40                  45

Val Ser Glu Leu Asp Arg Glu Val Thr Arg Leu Pro Ser Asp Leu Lys
    50                  55                  60

Asp Thr Glu Gly Asn Asn Val Gly Asp Tyr Val Lys Gly Gly Leu Glu
65                  70                  75                  80

Lys Ala Leu Thr Asp Glu Lys Val Gly Leu Asn Asn Thr Pro Lys Ala
                85                  90                  95

Leu Asp Thr Ala Pro Lys Ala Leu Asp Thr Ala Leu Asn Glu Leu Gly
            100                 105                 110

Pro Asp Gly Asp Glu Glu Glu
        115

<210> SEQ ID NO 28
<211> LENGTH: 96
<212> TYPE: PRT
<213> ORGANISM: Streptococcus pneumoniae

<400> SEQUENCE: 28

Gln Ala Leu Tyr Glu Ser Thr Gln Glu Gln Ile Glu Glu Leu Lys Asp
1               5                   10                  15

```
Tyr Asn Glu Gln Ile Ser Glu Gly Glu Glu Thr Leu Ile Leu Ala Ile
            20              25              30

Gln Asn Lys Ile Ser Asp Leu Asp Asp Lys Ile Ala Glu Ala Glu Lys
        35              40              45

Lys Leu Ala Asp Ser Gln Asn Gly Glu Gly Val Glu Asp Tyr Trp Thr
    50              55              60

Ser Gly Asp Glu Asp Lys Leu Glu Lys Leu Gln Ala Glu Gln Asp Glu
65              70              75              80

Leu Gln Ala Glu Leu Asp Gln Leu Leu Asp Glu Val Asp Gly Gln Glu
                85              90              95
```